United States Patent
Miller et al.

(10) Patent No.: US 7,125,542 B2
(45) Date of Patent: Oct. 24, 2006

(54) METHODS AND COMPOSITIONS FOR TREATING CONDITIONS OF THE EYE

(75) Inventors: Joan W. Miller, Winchester, MA (US); Evangelos S. Gragoudas, Lexington, MA (US); Reem Z. Renno, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 09/780,142

(22) Filed: Feb. 9, 2001

(65) Prior Publication Data

US 2002/0040015 A1    Apr. 4, 2002

Related U.S. Application Data

(60) Provisional application No. 60/181,641, filed on Feb. 10, 2000.

(51) Int. Cl.
  *A61K 39/395*   (2006.01)
  *A61K 38/41*   (2006.01)
  *A61K 38/18*   (2006.01)
  *A01N 55/02*   (2006.01)

(52) U.S. Cl. ............ 424/9.61; 514/184; 514/410; 514/453; 514/454; 424/145.1; 424/184.1

(58) Field of Classification Search ............... 424/9.61; 514/185, 912, 410
See application file for complete search history.

(56) References Cited

U.S. PATENT DOCUMENTS

| | | | |
|---|---|---|---|
| 5,171,749 A | | 12/1992 | Levy et al. |
| 5,707,986 A | * | 1/1998 | Miller et al. |
| 5,733,876 A | * | 3/1998 | O'Reilly et al. |
| 5,798,349 A | | 8/1998 | Levy et al. |
| 5,854,205 A | | 12/1998 | O'Reilly et al. |
| 6,117,862 A | | 9/2000 | Margaron et al. |
| 6,162,242 A | * | 12/2000 | Peyman et al. |
| 6,180,402 B1 | | 1/2001 | Granville et al. |
| 6,225,303 B1 | | 5/2001 | Miller et al. |
| 6,270,749 B1 | * | 8/2001 | Blumenkranz et al. |
| 6,331,523 B1 | | 12/2001 | Kljavin et al. |
| 6,342,219 B1 | * | 1/2002 | Thorpe et al. ........... 424/145.1 |
| 6,899,723 B1 | | 5/2005 | Chen |
| 2002/0049247 A1 | | 4/2002 | Chen |
| 2003/0171320 A1 | | 9/2003 | Guyer et al. |
| 2003/0175282 A1 | | 9/2003 | Miller et al. |
| 2003/0185834 A1 | | 10/2003 | Miller et al. |
| 2004/0167091 A1 | | 8/2004 | Guyer et al. |
| 2005/0043220 A1 | | 2/2005 | Guyer et al. |

FOREIGN PATENT DOCUMENTS

| | | |
|---|---|---|
| WO | WO 95 24930 A | 9/1995 |
| WO | WO 97/05127 | 2/1997 |
| WO | WO 97 33619 A | 9/1997 |
| WO | WO 97 45450 A | 12/1997 |
| WO | WO 98 25648 A | 6/1998 |
| WO | WO 99 03503 A | 1/1999 |
| WO | WO 00/40089 | 7/2000 |
| WO | WO 00 51638 | 9/2000 |
| WO | WO 01 51087 A | 7/2001 |
| WO | WO 01/58240 | 8/2001 |
| WO | WO 03/039404 | 5/2003 |

OTHER PUBLICATIONS

Verma et al., Nature 389: 239-242, Sep. 1997.*
Ngo et al., 1994, The Protein Folding Problem and Tertiary Structure Prediction, pp. 492-495.*
Adamis et al, Arch Ophthalmol 114(1): 66-71, Jan. 1996.*
Kramer et al, Ophthalmology 103(3): 427-38, Mar. 1996.*
Adamis et al. "Inhibition of Vascular Endothelial Growth Factor Prevents Retinal Ischemia—Associated Iris Neovascularization in a Nonhuman Primate" (1996) *Arch Ophthalmol*, vol. 114, pp. 66-71.
Ahmad et al "Photodynamic Therapy Results in Induction of WAF1/C1P1/P21 Leading to Cell Cycle Arrest and Apoptosis" (1998) *Proc. Natl. Acad. Sci. USA*, vol. 95, pp. 6977-6982.
Allen et al. "Photodynamic Therapy: Tumor Targeting with Adenoviral Proteins" (1999) *Photochemistry and Photobiology*, vol. 70, No. 4, pp. 512-523.
Akhlynina et al. "Insulin-mediated Intracellular Targeting Enhances the Photodynamic Activity of Chlorine$_6$" (1995) *Cancer Research*, vol. 55, pp. 1014-1019.
Arenberg et al."Interferon-y-inducible Protein 10 (IP-10) Is an Angiostatic Factor That Inhibits Human Non-small Cell Lung Canter (NSCLC) Tumorigenesis and Spontaneous Metastases" (1996) *J. Exp. Med.* vol. 184, pp. 981-992.
Ball et al. "A Comparative Study of the Cellular Uptake and Photodynamic Efficacy of Three Novel Zinc Phthalocyanines of Differing Charge" (1999) *Photochemistry and Photobiology*, vol. 69, No.3, pp. 390-396.
Berg, K. and Moan, J. "Lysosomes and Microtubules as Targets for Photochemotherapy of Cancer" (1997) *Photochemistry and Photobiology*, vol. 65, No. 3, pp. 403-409.
Biolo et al. "Effect of Photosensitizer Delivery System and Irradiation Parameters on the Efficiency of Photodynamic Therapy of B16 Pigmented Melanoma in Mice" (1996) *Photochemistry and Photobiology*, vol. 63, No. 2, pp. 224-228.
Birchler M et al. "Selective Targeting and Photocoagulation of Ocular Angiogenesis Mediated by a Phage-derived Human antibody Fragment" (1999) *Nature Biotechnology*, vol. 17, No. 10, pp. 984-988.

(Continued)

*Primary Examiner*—Christina Chan
*Assistant Examiner*—Phuong Huynh
(74) *Attorney, Agent, or Firm*—Goodwin Procter LLP

(57) ABSTRACT

Provided are methods and compositions for the photodynamic therapy (PDT) of ocular conditions characterized by the presence of unwanted choroidal neovasculature, for example, neovascular age-related macular degeneration. The selectivity and sensitivity of the PDT method can be enhanced by combining the PDT with an anti-angiogenesis factor, for example, angiostatin or endostatin, or with an apoptosis-modulating factor. Furthermore, the selectivity and sensitivity of the PDT may be further enhanced by coupling a targeting moiety to the photosensitizer so as to target the photosensitizer to choroidal neovasculature.

11 Claims, 6 Drawing Sheets

OTHER PUBLICATIONS

Brem et al. "The Combination of Antiangiogenic Agents to Inhibit Primary Tumor Growth and Metastasis" (1993) *J. Ped. Surgery*, vol. 28, No. 10, pp. 1253-1257.
Bressler, et al. "Age-related Macular Degeneration" (1998) *Survey of Ophthalmology*, vol. 32, No. 6, pp. 375-413.
Brooks et al. "Integrin $\alpha_v\beta_3$ Antagonists Promote Tumor Regression by Inducing Apoptosis of Angiogenic Blood Vessels" (1994) *Cell*, vol. 79, pp. 1157-1164.
Brooks et al. "Requirement of Vascular Integrin $\alpha_v\beta_3$ for Angiogenesis" (1994) *Science*, vol. 264, pp. 569-571.
Ciardiello et al. "Antitumor Activity of Combined Blockade of Epidermal Growth Factor Receptor and Protein Kinase A" (1996) *J. Natl. Can. Inst.*, vol. 88, No. 23, pp. 1770-1776.
Ciulla T A et al. "Changing Therapeutic Paradigms for Exudative Age-related Macular Degeneration: Antiangiogenic Agents and Photodynamic Therapy" (1999) *Expert Opinion on Investigational Drugs, Ashley Publications LTD*, vol. 8, No. 12, pp. 2173-2182.
D'Amato et al. "Thalidomide is an Inhibitor of Angiogenesis" (1994) *Proc. Natl. Acad. Sci. USA*, vol. 91, pp. 4082-4085.
Dimitroff C J et al. "Anti-Angiogenic Activity Of Selected Receptor Tyrosine Kinase Inhibitors, PD166285 And PD173074: Implications For Combination Treatment With Photodynamic Therapy" (1999) *Investigational New Drugs*, vol. 17, No. 2, pp. 121-135.
Dobi et al. "A New Model of Experimental Choroidal Neovascularization in the Rat" (1989) *Arch Ophthalmol*, vol. 107, pp. 264-269.
Dougherty et al. "Photodynamic Therapy" (1998) *J. Natl. Can. Inst.*, vol. 90, No. 12, pp. 889-905.
Ellerby et al. "Anti-cancer activity of targeted pro-apoptotic peptides" (1999) *Nature Medicine*, vol. 5, No. 9, pp. 1032-1038.
Ferrario et al. "Antiangiogenic Treatment Enhances Photodynamic Therapy Responsiveness in a Mouse Mammary Carcinoma" (2000) *Cancer Research*, vol. 60, No. 15, pp. 4066-4069.
Fingar et al. "Analysis of Acute Vascular Damage After Photodynamic Therapy Using Benzoporphyrin Derivative (BPD)" (1999) *British Journal of Cancer*, vol. 79, pp. 1702-1708.
Folkman, J. "Angiogenesis in Cancer, Vascular, Rheumatoid and Other Disease" (1995) *Nature Medicine*, vol. 1, pp. 27-31.
Friedlander et al. "Definition of Two Angiogenic Pathways by Distinct $\alpha_v$ Integrins"(1995) *Science*, vol. 270, pp. 1500-1502.
Friedlander et al. "Involvement of Integrins $\alpha_v\beta_3$ and $\alpha_v\beta_5$ in Ocular Neovascular Diseases" (1996) *Pro. Natl. Acad. Sci. USA*, vol. 93, pp. 9764-9769.
Granville et al. "Overexpression of Bcl-$X_L$ Prevents Caspase-3-mediated Activation of DNA Fragmentation Factor (DFF) Produced by Treatment with the Photochemotherapeutic Agent BPD-MA" (1998) *FEBS Letters*, vol. 422, pp. 151-154.
Granville et al. "Rapid cytochrome *c* Release, Activation of Caspases 3, 6, 7 and 8 Followed by Bap31 Cleavage in HeLa cells Treated with Photodynamic Therapy" (1998) *FEBS Letters*, vol. 437, pp. 5-10.
Gupta et al. "Involvement of Nitric Oxide During Phthalocyanine (Pc4) Photodynamic Therepy-Mediated Apoptosis" (1998) *Cancer Research*, vol. 58, pp. 1785-1788.
Guyer et al. "Subfoveal Choroidal Neovascular Membranes in Age-Related Macular Degeneration" (1986) *Arch Ophthalmol*, vol. 104, pp. 702-705.
Hakem et al. "Differential Requirement for Caspase 9 in Apoptotic Pathways in Vivo" (1998) *Cell*, vol. 94, pp. 339-352.
Hanahan, D. and Folkman, J. "Patterns and Emerging Mechanisms of the Angiogenic Switch during Tumorigenesis" (1996) *Cell*, vol. 86, pp. 353-364.
He et al. "Photodynamic Therapy with Photofrin II Induces Programmed Cell Death in Carcinoma Cell Lines" (1994) *Photochemistry and Photobiology*, vol. 59, No. 4, pp. 468-473.
He et al. "The Induction of Partial Resistance to Photodynamic Therapy by the Protooncogene *BCL-2*" (1996) *Photochemistry and Photobiology*, vol. 64, No. 5, pp. 845-852.
He et al. "Variation in Photodynamic Efficacy during the Cellular Uptake of Two Phthalocyanine Photosensitizers" (1998) *Photochemistry and Photobiology*, vol. 67, No. 6, pp. 720-728.
Hockenbery et al. "Bcl-2 Functions in an Antioxidant Pathway to Prevent Apoptosis" (1993) *Cell*, vol. 75, pp. 241-251.
Hunt David W.C. et al. "Impact of PDT and Fas-mediated Apoposis on Cells of the System" (1998) *Photochemistry and Photobiology*, vol. 67, Spec. Issue, pp. 69S.
Husain et al. "Photodynamic Therapy." (Age-Related Macular Degeneration),Chapter 17, pp. 297-307.
Husain, et al. "Intravenous Infusion of Liposomal Benzoporphyrin Derivative for Photodynamic Therapy of Experimental Choroidal Neovascularization" (1996) *Arch Ophthalmol*, vol. 114, pp. 978-985.
Hyman et al. "Senile Macular Degeneration: A Case-Control Study" (1983) *American Journal of Epidemiology*, vol. 118, No. 2., pp. 213-227.
Ingber et al. "Synthetic Analogues Of Fumagillin That Inhibit Angiogenesis and Suppress Tumour Growth" (1990) *Nature*, vol. 348, pp. 555-557.
Kane et al. "Bcl-2 Inhibition of Neural Death: Decreased Generation of Reactive Oxygen Species" (1993) *Science*, vol. 262, No. 19, pp. 1274-1277.
Kerr, et al. "Apoptosis: A Basic Biological Phenomenon with Wide-Ranging Implications in Tissue Kinetics" (1972) *Br. J. Cancer*, vol. 26, pp. 239-257.
Kessel et al. "Biodistribution of Photosensitizing Agents" (1993) *Int. J. Biochem*, vol. 25, No. 10, pp. 1377-1383.
Kessel, D. and Luo, Y. "Photodynamic therapy: A Mitochondrial Inducer of Apoptosis" (1999) *Cell Death and Differentiation*, vol. 6, pp. 28-35.
Klein, B. and Klein, R. "Cataracts and Macular Degeneration in Older Americans" (1982) *Arch Ophthalmol*, vol. 100, pp. 571-573.
Kramer, et al. "Liposomal Benzoporphyrin Derivative Verteporfin Photodynamic Therapy" (1996) *Ophthalmology*, vol. 103, No. 3, pp. 427-438.
Kroemer, G. "The Proto-oncogene Bcl-2 and Its Role in Regulating Apoptosis" (1997) *Nature Medicine*, vol. 3, No. 6, pp. 614-620.
Lucas et al. "Multiple Forms of Angiostatin Induce Apotosis in Endothelial Cells" (1998) *Blood*, vol. 92, No. 12, pp. 4730-4741.
Luo et al. "The Role of Mitochondrial Photodamage in PDT-induced Apoptosis" (1998) *Chemical Abstracts* vol. 129, No. 13, & *Proc. Spie-Int. Soc. Opit. Eng.* vol. 3247, pp. 112-117.
Mauceri et al. "Combined effects of Angiostatin and Ionizing Radiation in Antitumour Therapy" (1998) *Nature*, vol. 394, pp. 287-291.
Miller et al. "Alternative Treatments of Neovascular Age-Related Macular Degeneration" (1999) Chapter 139, pp. 2014-2027.
Miller JW et al. "Photodynamic Therapy of Experimental Chorodial Neovascularization Using Lipoprotein-deliver Benzoporphyrin" (1995) *Archives of Opthalmology*, vol. 113, No. 6, pp. 810-818.
Mori et al. "Photodynamic Therapy for Experimental Tumors Using ATX-S10(Na), a Hydrophilic Chlorin Photosensitizer, and Diode Laser." (2000) *Jpn. J. Cancer*, vol. 91, No. 7, pp. 753-759.
Moser et al. "Angiostatin binds ATP Synthase on the Surface of Human Endothelial Cells" (1999) *Proc. Natl Acad. Sci USA*, vol. 96, pp. 2811-2816.
Mosmann, T. "Rapid Colorimetric Assay for Cellular Growth and Survival: Application to Proliferation and Cytotoxicity Assays" (1983) *Journal of Immunological Methods*, vol. 65, pp. 55-63.
Netland et al. "In situ Labelling of Vascular Endothelium with Fluorescent Acetylated Low Density Lipoprotein" (1985) *Histochem J.*, vol. 17, pp. 1309-1320.
Nicholson, D. and Thornberry, N. "Capases: Killer Proteases" (1997) *TIBS*, vol. 22, pp. 299-306.
Obana et al. "Selective Occlusion of Choroidal Neovascularization by Photodynamic Therapy with a Water-Soluble Photosensitizer, ATX-S10" (1999) *Lasers Surg. Med.*, vol. 24, No. 3, pp. 209-222.
Obana et al. "Selective Photodynamic Effects of the New Photosensitizer ATX-S10(Na) on Choroidal Neovascularization in Monkeys" (2000) *Arch. Ophthalmol.* vol. 118, No. 5, pp. 650-658.
Okamoto et al. "Animal Model: Transgenic Mice with Increased Expression of Vascular Endothelial Growth Factor in the Retina" (1997) *Amer. J. Path.* vol. 151, No. 1, pp. 281-291.

Oleinick et al. "The Photobiology of Photodynamic Therapy: Cellular Targets and Mechanisms" (1998) *Radiation Research*, 150 (Suppl.), pp. S146-S156.

O'Reilly et al. "Angiostatin Induces and Sustains Dormancy of Human Primary Tumors In Mice" (1996) *Nature Medicine*, vol. 2, No. 6, pp. 689-692.

O'Reilly et al. "Angiostatin: A Novel Angiogenesis Inhibitor That Mediates the Suppression of Metastases by a Lewis Lung Carcinoma" (1994) *Cell*, pp. 315-328.

O'Reilly et al. "Endostatin: An Endogenous Inhibitor of Angiogenesis and Tumor Growth" (1997) *Cell*, vol. 88, pp. 277-285.

Pidgeon & Colles et al. "Recent Developments In Tunable Lasers For Spectroscopy" (1979) *Nature*, vol. 279, pp. 377-381.

Pollack et al. "Repair of Retinal Pigment Epithelium and Choriocapillaries After Laser Photocoagulation: Correlations Between Scanning Electron, Transmission Electron and Light Microscopy" (1997) *Opthal. Res.*, vol. 29, pp. 393-404.

Reddi, E. "Role of Delivery Vehicles for Photosensitizers in the Photodynamic Therapy of Tumors" (1997) *J. Photochem & Photobiol.* vol. 37, pp. 189-195.

Renno et al. "Photodynamic Therapy Using Lu-Tex Induces Apoptosis in Vitro, and its Effect is Potentiated by Angiostatin in Retinal Capillary Endothelial Cells" (2000) *Inves. Ophthal. & Vis. Sci*, vol. 41, No. 12, pp. 3963-3971.

Ryan "Subretinal Neovascularization: Natural History of an Experimental Model" (1982) *Arch Ophthalmol.* vol. 100, pp. 1804-1809.

Schmidt-Erfurth, U. et al. "Photodynamic therapy in Ocular Vascular Disease" (1998) *Laser Phys.*, vol. 8, No. 1, pp. 191-198.

Senior, K. "Ageing eyes retain their mystery." (1999) *The Lancet* vol. 353, pp. 818.

Separovic et al "Association of Ceramide Accumulation with Photodynamic Treatment-Induced Cell Death" (1998) *Photochemistry and Photobiology*, vol. 68, No. 1, pp. 101-109.

Sharma A. et al. "Combination of Photodynamic Therapy and Angiogenic Therapy for the Treatment of Human Breast Cancer in Nude Athymic Myce" (1996) *Proceedings of the Annual Meeting of the American Association for Cancer Research*, US, Phildelphia, AACR, vol. Meeting 87, pp. 291.

Stellmach et al. "Prevention of Ischemia-Induced Retinopathy by the Natural Ocular Antiangiogenc Agent Pigment Epithelium-Derived Factor" (2000) *Proc. Natl. Acad. Sci.* pp. 1-5.

Tolentino et al. "Vascular Endothelial Growth Factor Is Sufficient to Produce Iris Neovascularization and Neovascular Glaucoma in a Nonhuman Primate" (1996) *Arch Ophthalmol*, vol. 114, pp. 964-969.

Varnes et al. "Photodynamic Therapy-Induced Apoptosis in Lymphoma Cells: Translocation of Cytochrome c Causes Inhibition of Respiration as Well as Caspase Activation" (1999) *Biochem. & Biophys. Res. Com.*, vol. 255, pp. 673-679.

Veis, et al. "Bcl-2-Deficient Mice Demonstrate Fulminant Lymphoid Apoptosis, Polycystic Kidneys, and Hypopigmented Hair" (1993) *Cell*, vol. 75, pp. 229-240.

Virgill et al. "Bcl-2 Overexpression in the HaCaT Cell Line is Associated with a Different Membrane Fatty Acid Composition and Sensitivity to Oxidative Stress" (1998) *Free Radical Biology & Medicine*, vol. 24, No. 1, pp. 93-101.

Voest et al. "Inhibition of Angiogenesis In Vivo by Interleukin 12" (1995) *J. Nat. Can. Inst.*, vol. 87, No. 8, pp. 581-586.

Vrouenraets, et al. "Targeting of a Hydrophilic Photosensitizer by Use of Internalizing Monoclonal Antibodies: A New Possibility for Use in Photodynamic Therapy" (2000) *Int. J. Cancer*, vol. 88, pp. 108-114.

Weishaupt et al. "Identification of Singlet Oxygen as the Cytotoxic Agent in Photo-inactivation of a Murine Tumor" (1976) *Can. Res.*, vol. 36, pp. 2326-2329.

West et al. "A Comparsion of the Sensitivity to Photodynamic Treatment of Endothelial and Tumour Cells in Different Proliferative States" (1990) *Int. J. Radiat. Biol.*, vol. 58, No. 1, pp. 145-156.

Woodburn et al. "Localization and Efficacy Analysis of the Phototherapeutic Lutetium Texaphyrin (PCI-0123) in the Murine EMT6 Sarcoma Model" (1997) *Photochemistry and Photobiology*, vol. 65, No. 3, pp. 410-415.

Young et al "Lutetium Texaphyrin (PCI-0123): A Near-Infrared, Water-Soluble Photosensitizer" (1996) *Photochemistry and Photobiology*, vol. 63, No. 6, pp. 892-897.

Zhang et al. "Antisense Bcl-2 Retrovirus Vector Increases the Sensitivity of a Human Gastric Adenocarcinoma Cell Line to Photodynamic Therapy" (1999) *Photochemistry and Photobiology*, vol. 69, No. 5, pp. 582-586.

Abels et al. "Targeting of the Tumor Microcirculation by Photodynamic Therapy with a Synthetic Porphycene" *J. Photochem. Photobiol. B.* (1997) 40(3): 305-12 Abstract.

Binétruy-Tournaire et al. "Identification of a Peptide Blocking Vascular Endothelial Growth Factor (VEGF)-mediated Angiogenesis" *EMBO Journal* (2000) 19(7): 1525-1533.

Brokx et al. "Designing Peptide-based Scaffolds as Drug Delivery Vehicles" *J. Control Release* (2002) 78(1-3): 115-23 Abstract.

Clauss et al. "Vascular Permeability Factor: A Tumor-derived Polypeptide that Induces Endothelial Cell and Monocyte Procoagulant Activity, and Promotes Monocyte Migration" *J. Exp. Med.* (1990) 172: 1535-1545.

Dolmans et al. "Targeting Tumor Vasculature and Cancer Cells in Orthotopic Breast Tumor by Fractionated Photosensitizer Dosing Photodynamic Therapy" *Cancer Res.* (2002) 62(15): 4289-94 Abstract.

Gruber et al. "Angiogenic Factors Stimulate Mast-Cell Migration" *Blood* (1995) 86(7): 2488-2493.

Guerrin et al. "Vasculotropin/Vascular Endothelial Growth Factor is an Autocrine Growth Factor for Human Retinal Pigment Epithelial Cells Cultured in Vitro" *J. Cell. Phys.* (1995) 164: 385-394.

Hackett et al. "Receptors for VEGF (flt-1 and flk-1) are Expressed in Nonvascular Cells in the Eye" *Invest. Ophthal. & Vis. Sci.* (1996) 37(3) Abstract.

Kamizuru et al. "Monoclonal Antibody-Mediated Drug Targeting to Choroidal Neovascularization in the Rat" Invest. *Ophthal. & Vis. Sci.* (2001) 42(11): 2664-2672.

Kim et al. "Constitutive Expression of VEGF, VEGFR-1, and VEGFR-2 in Normal Eyes" *Invest. Ophthal. & Vis. Sci.* (1999) 40(9): 2115-2121.

Konan et al. "State of the Art in the Delivery of Photosensitizers for Photodynamic Therapy" *J. Photochem. Photobiol. B.* (2002) 66(2): 89-106 Abstract.

Koukourakis et al. "Clinical and Experimental Evidence of Bcl-2 Involvement in the Response to Photodynamic Therapy" *Anticancer Research* (2001) 21: 663-668.

Lachgar et al. "Vascular Endothelial Growth Factor is an Autocrine Growth Factor for Hair Dermal Papilla Cells" *J. Invest. Dermatology* (1996) 106(1): 17-23.

Lange et al. "A New Drug-Screening Procedure for Photosensitizing Agents Used in Photodynamic Therapy for CNV" *Invest. Ophthal. & Vis. Sci.* (2001) 42(1): 38-46.

Miller Photodynamic Therapy for Choroidal Neovascularization The Jules Gonin Lecture, Montreux, Switzerland, 1 *Springer-Verlag 2003* (2002).

Miller et al. "Targeted Photodynamic Therapy of Experimental Choroidal Neovascularization Using Verteporfin and a Homing Peptide to VEGF-R2" *Program from Retina Congress*, San Francisco 2002.

Nagae et al. "Selective Targeting and Photodynamic Destruction of Intimal Hyperplasia by Scavenger-receptor Mediated Protein-chlorin e6 Conjugates" *J. Cardiovasc. Surg.* (1998) 39(6): 709-15 Abstract.

Ortega et al. "Activation of the VEGF Receptor flt-1 Mediates Corneal Endothelial Cell Migration and Permeability" *Invest. Ophthal & Vis. Sci.* (1996) 37(3) Abstract.

O'Schlingemann et al. "Role of Vascular Permeability Factor/Vascular Endothelial Growth Factor in Eye Disease" *Br. J. Ophthal.* (1997) 81: 501-512.

Qualls et al. "Chloroaluminum Phthalocyanine Tetrasulfonate Delivered via Acid-labile Diplasmenylcholine-folate Lipsomes: Intracellular Localization and Synergistic Phototoxicity" *Int. J. Cancer* (2001) 93(3): 384-92 Abstract.

Renno et al. "Selective Targeting of Verteporfin to Choroidal Neovascularization Mediated by a Homing Peptide to VEGF-R2" *Abstract of presentation at Association for Research in Vision and Ophthalmology 2002 Meeting.*

Rosenkranz et al. "Targeted Intracellular Delivery of Photosensitizers to Enhance Photodynamic Efficiency" *Immun. and Cell Biology* (2000) 78: 452-464.

Schmidt-Erfurth et al. "Photodynamic Targeting of Human Retinoblastoma Cells Using Covalent Low-density Lipoprotein Conjugates" *Br. J. Cancer* (1997) 75(1): 54-61.

Shiah et al. "Antitumor Activity of $N$-(2-Hydroxypropl)methacrylamide Copolymer-Mesochlorin $e_6$ and Adriamycin Conjugates in Combination Treatments[1]" *Clin. Cancer Research* (2000) 6: 1008-1015.

Takagi et al. "Hypoxia Regulates Vascular Endothelial Growth Factor Receptor *KDR/Flk* Gene Expression Through Adenosine $A_2$ Receptors in Retinal Capillary Endothelial Cells" *Invest. Ophthal. & Vis. Sci.* (1996) 37(7): 1311-1321.

Takagi et al. "Identification and Characterization of Vascular Endothelial Growth Factor Receptor (Flt) in Bovine Retinal Pericytes" *Diabetes* (1996) 45: 1016-1023.

Takahashi et al. "Protein Tyrosine Kinases Expressed in Glomeruli and Cultured Glomerular Cells: flt-1 and VEGF Expression in Renal Mesangial Cells" *Biochem and Biophys. Res. Comm.* (1995) 209(1): 218-226.

Terada et al. "Modified Verteporfin Photodynamic Therapy (PDT), PDT Combined with Angiostatin *In Vitro* and *In Vivo*" *Abstract of presentation at Association for Research in Vision and Ophthalmology 2002 Meeting.*

Terada et al. "Enhanced Photodynamic Therapy Using Angiostatin with Verteporfin PDT in a Laser-injury Rat Model" *Abstract to be presented at Association for Research in Vision and Ophthalmology 2003 Meeting.*

Tolentino et al. "Angiography of Fluoresceinated Anti-Vascular Endothelial Growth Factor Antibody and Dextrans in Experimental Choroidal Neovascularization" *Arch. Ophthalmol.* (2000) 118: 78-84.

Vrouenraets et al. "Comparison of Aluminum (III) Phthalocyanine Tetrasulfonate- and Meta-tetrahydroxyphenylchlorin-monoclonal Antibody Conjugates for their Efficacy in Photodynamic Therapy in Vitro" *Int. J. Cancer* (2002) 98(5): 793-8 Abstract.

Yang et al. "Flk-1. a Receptor for Vascular Endothelial Growth Factor (VEGF), is Expressed by Retinal Progenitor Cells" *J. Neurosci.* (1996) 16(19): 6089-6099.

"A Clinical Trial to Evaluate the Effect of an Experimental Compound on Reducing the Number of Retreatments Required in Photodynamic Therapy (PDT) with Visudyne™," Alcon web site, http://www.alconlabs.com/us/co/c-00-07study.ihtml (printed Apr. 4, 2003).

Adamis, "Looking Forward: Ocular Biochemical Warfare—The VEGF Attack," American Academy of Ophthalmology Meeting (Retina, Giant Steps: A Look at the Past—An Eye on the Future) Subspecialty Day (The Wet Story: Exudative Age-Related Macular Degeneration) Presentation, Orlando, Fla. (Oct. 18-19, 2002).

Behling et al., "Adeno-associated Delivery of TIMP-3 Inhibits Experimental Choroidal Neovascularization," *Invest. Ophthalmol Vis Sci.* 44: E-Abstract 1425 (2003).

Blumenkranz et al., "Verteporfin therapy for subfoveal choroidal neovascularization in age-related macular degeneration: three-year results of an open-label extension of 2 randomized clinical trials—TAP Report No. 5," *Arch Ophthalmol.* 120(10):1307-14 (Oct. 2002).

Bressler, "Photodynamic Therapy for AMD: Re-treatment Considerations," American Academy of Ophthalmology Meeting (Retina, Giant Steps: A Look at the Past—An Eye on the Future) Subspecialty Day (The West Story: Exudative Age-Related Macular Degeneration) Presentation, Orlando, Fla. (Oct. 18-19, 2002).

Campochiaro et al., "The pathogenesis of choroidal neovascularization in patients with age-related macular degeneration," *Molecular Vision* 5: 34-8 (Nov. 3, 1999).

Ciulla et al., "Age-Related Macular Degeneration: A Review of Experimental Treatments," *Surv. Ophthalmol.* 43(2): 134-46 (1998).

Corjay et al., "alpha$_v$beta$_3$, alpha$_v$Beta$_5$, and Osteopontin Immunostaining in Experimental Choroidal Neovascularization in the Monkey," Presentation #4473, Abstract on p. S965.

Csaky, K., "Anti-vascular endothelial growth factor therapy for neovascular age-related macular degeneration: promises and pitfalls (Comment)," *Ophthalmology* 110(5):879-81 (May 2003).

Dahlin et al., "Design of a Specialized Cannula for Poseterior Juxtascleral Delivery of Anecortave Acetate to the Retina for Treatment CNV Associated with Age-Related Macular Degeneration," *Invest. Ophthalmol Vis Sci.* 44: E-Abstract 5036 (2003).

Danis, "Pharmacotherapy for AMD: The Role of Intravitreal Steroids and Related Agents," American Academy of Ophthalmology Meeting (Retina, Giant Steps: A Look at the Past—An Eye on the Future) Subspecialty Day (The Wet Story: Exudative Age-Related Macular Degeneration) Presentation, Orlando, Fla. (Oct. 18-19, 2002).

de Juan, "Surgery for AMD: Limited Translocation in the Era of Photodynamic Therapy," American Academy of Ophthalmology Meeting (Retina, Giant Steps: A Look at the Past—An Eye on the Future) Subspecialty Day (The Wet Story: Exudative Age-Related Macular Degeneration) Presentation, Orlando, Fla. (Oct. 18-19, 2002).

Eyetech Study Group, "Anti-vascular endothelial growth factor therapy for subfoveal choroidal neovascularization secondary to age-related macular degeneration: phase II study results," *Ophthalmology* 110(5):979-86 (May 2003).

Gallemore et al., "AMD Treatment Update: Along with Visudyne and TTT, injectable anti-angiogenesis agents are on the forefront of current research," *Ophthalmology Management,* 69-72 (Mar. 2003).

Gauthier et al., "Safety and Efficacy of Intravitreal Injection of rhuFab V2, an Anti-vascular Endothelial Growth Factor (VEGF) in Combination With Verteporfin PDT on Experimental Choroidal Neovascularization," *ARVO Poster*.

Gauthier et al., "Safety and Efficacy of Intravitreal Injection of rhuFab VEGF in Combination With Verteporfin PDT on Experimental Choroidal Neovascularization," *ARVO, The Association for Research in Vision and Ophthalmology* (Oasis, Online Abstract Submission and Invention System, Program Planner, Presentation # 566).

Granville et al., "Fas ligand and TRAIL augment the effect of photodynamic therapy on the induction of apoptosis in JURKAT cells," *International Immunopharmacolgy* 1: 1831-40 (2001).

Guyer, D.R., "Pharmacotherapy for AMD: VEGF Inhibitors and Related Agents," American Academy of Ophthalmology Meeting (Retina, Giant Steps: A Look at the Past—An Eye on the Future) Subspecialty Day (The Wet Story: Exudative Age-Related Macular Degeneration) Presentation, Orlando, Fla. (Oct. 18-19, 2002).

Haimovici et al., "Localization of Lipoprotein-delivered benzoporphyrin derivative in the rabbit eye," *Curr. Eye Res.* 16(2):83-90 (1997).

Heier et al., "rhuFAB V2 (an Anti-VEGF Antibody Fragment) in Neovascular AMD: Safety and Tolerability of Multiple Intravitreal Injections—Preliminary Data from a Single Center," *ARVO Poster*.

Husain et al., "Effects of Photodynamic Therapy Using Verteporfin on Experimental Choroidal Neovasculaturization and Normal Retina and Choroid up to 7 Weeks after Treatment," *Invest. Ophthalmol Vis Sci.* 40(10): 2322-31 (1999).

Husain et al., Photodynamic therapy and digital angiography of experimental iris neovascularization using liposomal benzoporphyrin derivative, *Ophthalmology* 104(8):1242-50 (Aug. 1997).

International Search Report for PCT/US01/04231 completed on Nov. 23, 2001.

Kaiser et al., "Five-Year Results of Verteporfin Therapy for Subfoveal CNV Due to AMD: Third Year of an Open-label Extension of the TAP Investigation," *Invest. Ophthalmol Vis Sci.* 44: E-Abstract 1099 (2003).

Kitchen et al., "Anecortave Acetate Monotherapy for the Treatment of Occult and Minimally Classic Choroidal Neovascularization in Age-related Macular Degeneration," *Invest. Ophthalmol Vis Sci.* 44: E-Abstract 5039 (2003).

Kliman et al., "Angiography and Photodynamic Therapy of Experimental Choroidal Neovascularization using Phthalocyanine Dye," Invest. Ophthalmol. Vis. Sci. (Suppl.) 30(3): 371 (1989).

Krzystolik et al., "Prevention of Experimental Choroidal Neovascularization With Intravitreal Anti-Vascular Endothelial Growth Factor Antibody Fragment," Arch. Ophthalomol. 120(2): 338-346 (2002).

Lai et al., "Suppression of Choroidal Neovascularization by Adeno-associated Virus Vector Expressing Angiostatin," Investigative Ophthalmology & Visual Science 42 (10): 2401-2407 (2001).

Leibowitz et al., "The Framingham Eye Study Monograph: An ophthalmological and epidemiological study of cataract, glaucoma, diabetic retinopathy, macular degeneration, and visual acuity in a general population of 2631 adults," Survey of Ophthalmology, Supplement (May-Jun. 1980).

Miller, "Photodynamic Therapy for AMD: Expanded Indications," American Academy of Ophthalmology Meeting (Retina, Giant Steps: A Look at the Past—An Eye on the Future) Subspecialty Day (The Wet Story: Exudative Age-Related Macular Degeneration) Presentation, Orlando, Fla. (Oct. 18-19, 2002).

Ngo et al., "Computational Complexity, Protein Structure Prediction, and Levinthal Paradox," Chapter 14 of The Protein Folding and Tertiary Structure Prediction, Merz and LeGrand, Eds., Burkhauser Boston, 1994.

Oleinick et al., "The role of apoptosis in response to photodynamic therapy: what, where, why, and how," Photochem. Photobiol. Sci. 1: 1-21 (2002).

Olsen et al., "An Evaluation of an Episcleral Anecortave Acetate Transscleral Drug Delivery System in Rhesus Monkey," Invest. Ophthalmol Vis Sci. 44: E-Abstract 4213 (2003).

Pasqualini et al., "Organ Targeting in Vivo using Phage display Peptide Libraries," Nature 380: 364-6 (1996).

Reinke et al., "Verteporfin photodynamic therapy retreatment of normal retina and choroid in the cynomolgus monkey," Ophthalmology 106(10):1915-23 (Oct. 1999).

Renno et al., "Expression of pigment epithelium-derived factor in experimental choroidal neovascularization," Invest Ophthalmol Vis Sci. 43(5):1574-80 (May 2002).

Renno et al., "Photodynamic therapy using Lu-Tex induces apoptosis in vitro, and its effect is potentiated by angiostatin in retinal capillary endothelial cells," Invest Ophthalmol Vis Sci. 41(12):3963-71 (Nov. 2000).

Renno et al., Photosensitizer delivery for photodynamic therapy of choroidal neovascularization. Adv Drug Deliv Rev. 52(1):63-78 (Oct. 31, 2001) Review.

Renno et al., "Selective photodynamic therapy by targeted verteporfin delivery to experimental choroidal neovascularization mediated by a homing peptide to vascular endothelial growth factor receptor-2," Arch Ophthalmol. 122(7):1002-11 (Jul. 2004).

Schlingemann et al., "Role of vascular permeability factor/vascular endothelial growth factor in eye disease," Br. J. Ophthalmol. 81: 501-12 (1997).

Schmidt-Erfurth et al., "Photodynamic therapy with verteporfin for choroidal neovascularization caused by age-related macular degeneration: results of retreatments in a phase 1 and 2 study," Arch Ophthalmol. 117(9):1177-87 (Sep. 1999). Erratum in: Arch Ophthalmol. 118(4):488 (Apr. 2000).

Sickenberg et al., "A preliminary study of photodynamic therapy using verteporfin for choroidal neovascularization in pathologic myopia, ocular histoplasmosis syndrome, angioid streaks, and idiopathic causes." Arch Ophthalmol. 118(3):327-36 (Mar. 2000).

Slakter et al., "Ancortave Acetate Administered as a Posterior Juxtascleral Injection for Subfoveal CNV in Age-Related Macular Degeneration (AMD-Climical Results)," Presentation at the Retina Congress 2002 Symposium (Sep. 8, 2002).

Slakter, "Pharmacotherapy for AMD: The Role of Periocular Steroids and Related Agents," American Academy of Ophthalmology Meeting (Retina, Giant Steps: A Look at the Past—An Eye on the Future) Subspecialty Day (The Wet Story: Exudative Age-Related Macular Degeneration) Presentation, Orlando, Fla. (Oct. 18-19, 2002).

Slakter et al., "Sub-Tenon's Administration of the Angiostatic Agent Anecortave Acetate in AMD Patients with Subfoveal Choroidal Neovascularization (CNV)—the Clinical Outcome," Invest. Ophthalmol Vis Sci. 44: E-Abstract 2909 (2002).

Slakter et al., "Verteporfin With Altered (Delayed) Light in Occult CNV (VALIO)—Results of a Phase II Controlled Clinical Trial," Invest. Ophthalmol Vis Sci. 44: E-Abstract 1101 (2003).

Trese, "Treatment of Neovascularization in ROP: Pharmacological Agents and the ERTOP Study," American Academy of Ophthalmology Meeting (Retina, Giant Steps: A Look at the Past—An Eye on the Future) Subspecialty Day (The Wet Story: Exudative Age-Related Macular Degeneration) Presentation, Orlando, Fla. (Oct. 18-19, 2002).

Verma et al., "Gene therapy—Promises, problems and prospects," Nature 389: 239-42 (Sep. 1997).

Yaacobi et al., "In-Vivo Studies with Trans-Scleral Anecortave Acetate Delivery Device Designed to Treat Choroidal Neovascularization in AMD," Invest. Ophthalmol Vis Sci. 44: E-Abstract 4210 (2003).

Zacks et al., "Caspase Activation in an Experimental Model of Retinal Detachment," Investigative Ophthalmology & Visual Science 44(3): 1262-7 (Mar. 2002).

Zacks et al., "Verteporfin Photodynamic Therapy in the Rat Model of Choroidal Neovascularization: Angiographic and Histologic Characterization," Investigative Ophthalmology & Visual Science 43 (0): 1-9 (2002).

Blaauwgeers et al., "Polarized Vascular Endothelial Growth Factor Secretion by Human Retinal Pigment Epithelium and Localization of Vascular Endothelial Growth Factor Receptors on the Inner Choriocapillaris," Am. J. Pathology 155(2): 421-428, 1999.

Husain et al., "Safety and Efficacy of Intravitreal Injection of Ranibizumab in Combination with Verteporfin PDT on Experimental Choroidal Neovascularization in the Monkey," Arch Opthalmol, 123: 509-516, 2005.

Witte et al., "Monoclonal antibodies targeting the VEGF receptor-2 (Flk/KDR) as an anti-angiogenic therapeutic strategy," Cancer and Metastasis Reviews 17: 155-161, 1998.

* cited by examiner

METHODS AND COMPOSITIONS FOR TREATING CONDITIONS OF THE EYE

REFERENCE TO RELATED APPLICATIONS

This application claims priority to U.S. Provisional Application Ser. No. 60/181,641, filed Feb. 10, 2000, the disclosure of which is incorporated herein by reference.

FIELD OF THE INVENTION

The invention relates generally to photodynamic therapy-based methods and compositions for treating ocular conditions and, more specifically, the invention relates to photodynamic therapy-based methods and compositions for treating ocular conditions characterized by unwanted choroidal neovasculature.

BACKGROUND

Choroidal neovascularization can lead to hemorrhage and fibrosis, with resulting visual loss in a number of conditions of the eye, including, for example, age-related macular degeneration, ocular histoplasmosis syndrome, pathologic myopia, angioid streaks, idiopathic disorders, choroiditis, choroidal rupture, overlying choroid nevi, and certain inflammatory diseases. One of the disorders, namely, age-related macular degeneration (AMD), is the leading cause of severe vision loss in people aged 65 and above (Bressler et al. (1988) SURV. OPHTHALMOL. 32, 375–413, Guyer et al. (1986) ARCH. OPHTHALMOL. 104, 702–705, Hyman et al. (1983) AM. J. EPIDEMIOL. 188, 816–824, Klein & Klein (1982) ARCH. OPHTHALMOL. 100, 571–573, Leibowitz et al. (1980) SURV. OPHTHALMOL. 24, 335–610). Although clinicopathologic descriptions have been made, little is understood about the etiology and pathogenesis of the disease.

Dry AMD is the more common form of the disease, characterized by drusen, pigmentary and atrophic changes in the macula, with slowly progressive loss of central vision. Wet or neovascular AMD is characterized by subretinal hemorrhage, fibrosis and fluid secondary to the formation of choroidal neovasculature (CNV), and more rapid and pronounced loss of vision. While less common than dry AMD, neovascular AMD accounts for 80% of the severe vision loss due to AMD. Approximately 200,000 cases of neovascular AMD are diagnosed yearly in the United States alone.

Currently there is no treatment for dry AMD. Until recently, laser photocoagulation has been the only therapy available for selected cases of neovascular AMD. Unfortunately, the majority of patients with neovascular AMD do not meet the criteria for laser photocoagulation therapy. Approximately 85% of patients with neovascular AMD have poorly defined, occult, or relatively extensive subfoveal choroidal neovascularization, none of which is amenable to laser therapy. In addition, laser photocoagulation relies on thermal damage to the CNV tissue, which damages the overlying neurosensory retina with consequent loss of visual function. Laser photocoagulation also is plagued by recurrences that occur in approximately 50% of cases.

Photodynamic therapy (PDT) has shown promising results as a new treatment for removing unwanted CNV and for treating neovascular AMD (Miller et al. (1999) ARCHIVES OF OPHTHALMOLOGY 117: 1161–1173, Schmidt-Erfurth et al. (1999) ARCHIVES OF OPHTHALMOLOGY 117: 1177–1187, TAP Study Group (1999) ARCHIVES OF OPHTHALMOLOGY 117: 1329–45, Husain et al. (1999) PHILADELPHIA: MOSBY; 297–307). PDT involves the systemic administration of a photosensitizer or PDT dye (photosensitizer) that accumulates in proliferating tissues such as tumors and newly formed blood vessels; followed by irradiation of the target tissue with low-intensity, non-thermal light at a wavelength corresponding to the absorption peak of the dye (Oleinick et al. (1998) RADIATION RESEARCH: 150: S146–S156). Excitation of the dye leads to the formation of singlet oxygen and free radicals-better known as reactive oxygen species which cause photochemical damage to the target tissue (Weishaupt et al. (1976) CANCER RES. 36: 2326–2329).

Studies using PDT for the treatment of CNV have demonstrated that, with the proper treatment parameters of photosensitizer dose, laser light dose, and timing of irradiation, relative selective damage to experimental CNV can be achieved, sparing retinal vessels, large choroidal vessels, and with minimal changes in the neurosensory retina (Husain et al. (1996) ARCH OPHTALMOL. 114: 978–985, Husain et al. (1997) SEMINARS IN OPHTHALMOLOGY 12: 14–25, Miller et al. (1995) ARCH OPHTHALMOL. 113: 810–818, Kramer et al. (1996) OPHTHALMOLOGY 103(3): 427–438). Moreover, a PDT-based procedure using a green porphyrin dye recently has been approved in a variety of countries for use in the treatment of neovascular AMD.

During clinical studies, however, it has been found that recurrence of leakage appears in at least a portion of the CNV by one to three months post-treatment. Increasing photosensitizer or light doses do not appear to prevent this recurrence, and can even lead to undesired non-selective damage to retinal vessels (Miller et al. (1999) ARCHIVES OF OPHTHALMOLOGY 117: 1161–1173). Several multicenter Phase 3 trials are underway to study repeated PDT treatments, applied every three months. The interim data look promising in terms of decreased rates of moderate vision loss (TAP Study Group (1999) ARCHIVES OF OPHTHALMOLOGY 117: 1329–45). The necessity for repeated PDT treatments can nevertheless be expected to lead to cumulative damage to the retinal pigment epithelium (RPE) and choriocapillaris, which may lead to progressive treatment-related vision loss.

Therefore, there is still a need for improved PDT-based methods that increase the efficacy and selectivity of treatment, and which reduce or delay a recurrence of the disorder.

SUMMARY OF THE INVENTION

The present invention is directed to PDT-based methods and compositions for treating ocular conditions associated with unwanted choroidal neovasculature. Such conditions include, for example, neovascular AMD, ocular histoplasmosis syndrome, pathologic myopia, angioid streaks, idiopathic disorders, choroiditis, choroidal rupture, overlying choroid nevi, and certain inflammatory diseases. The invention provides a more effective PDT-based method for treating unwanted CNV that has one or more of the following advantages: increased efficacy of treatment; increased selectivity for CNV; and reduced or delayed recurrence of the condition following PDT.

In one aspect, the invention provides a method of treating unwanted CNV in a mammal, wherein the CNV comprises endothelial cells, for example, capillary endothelial cells. The method comprises the steps of: (a) administering to the mammal, for example, a primate, preferably, a human, an anti-angiogenesis factor in an amount sufficient to permit an effective amount to localize in the CNV; (b) administering to the mammal an amount of a photo sensitizer (PDT dye) sufficient to permit an effective amount to localize in the CNV; and (c) irradiating the CNV with laser light such that the light is absorbed by the photosensitizer so as to occlude the CNV. During practice of this method, the damage to endothelial cells disposed within the choroidal neovasculature is greater than the damage experienced by endothelial cells in a similar treatment lacking administration of the anti-angiogenesis factor. Furthermore, the anti-angiogenesis factor can potentiate the cytotoxicity of PDT. For example, the anti-angiogenesis factor and the PDT may act synergistically to selectively kill capillary endothelial cells, while at the same time sparing retinal cells, for example, retinal pigment epithelial cells and cells disposed in the neurosensory retina, for example, photoreceptor cells and Mueller cells.

The anti-angiogenesis factor can enhance the selectivity of the PDT by, for example, occluding the CNV while at the same sparing surrounding blood vessels, for example, normal choroidal and retinal vasculature, and/or tissue, for example, the overlying neurosensory retina. Accordingly, inclusion of the anti-angiogenesis factor makes the PDT method more selective for capillary endothelial cells. Furthermore, practice of the invention can slow down or delay the recurrence of choroidal neovasculature.

A variety of anti-angiogenesis factors may be used in the invention. Useful anti-angiogenesis factors, include, for example: angiostatin; endostatin; a peptide containing a RGD tripeptide sequence and capable of binding the $\alpha v\beta$ integrin; a COX-2 selective inhibitor; halofuginone; anecotave acetate; antibodies and other peptides that bind vascular endothelial growth factor receptor; antibodies, other peptides, and nucleic acids that bind vascular endothelial growth factor to prevent or reduce its binding to its cognate receptor; tyrosine kinase inhibitors; thrombospondin-1; anti-epidermal growth factor; hepatocyte growth factor; thromboxane; and pigment endothelial-derived growth factor. Preferred anti-angiogenic factors include angiostatin, endostatin and pigment epithelium-derived growth factor.

The anti-angiogenesis factor may, under certain circumstances, be co-administered simultaneously with the photosensitizer. In a preferred embodiment, however, the anti-angiogenesis factor is administered to the mammal prior to administration of the photosensitizer.

In another aspect, the invention provides a method of treating unwanted CNV in a mammal. The method comprises the steps of: (a) administering to a mammal, for example, a primate, preferably, a human, an amount of a photosensitizer to permit an effective amount to localize in the CNV, the photosensitizer comprising a targeting moiety that binds preferentially to cell surface ligands disposed on endothelial cells, for example, capillary endothelial cells, present in the CNV; and (b) irradiating the CNV with laser light such that the light is absorbed by the photosensitizer so as to occlude the CNV. The targeting moieties bind preferentially to CNV and, therefore, can increase the effective concentration of photosensitizer in the CNV relative to surrounding cells and tissues. Accordingly, such a method increases the selectivity of the PDT method for CNV while sparing surrounding retinal and large choroidal blood vessels and overlying neurosensory retina.

The targeting moiety can be any molecule, for example, a protein, peptide, nucleic acid, peptidyl-nucleic acid, organic molecule or inorganic molecule that has an affinity for endothelial cells within CNV. However, targeting proteins and peptides are preferred. For example, the targeting peptide can be a peptide that targets $\alpha v\beta$ integrin, for example, $\alpha v\beta$ 3 integrin or $\alpha v\beta$ 5 integrin. Alternatively, the targeting peptide can be an antibody, for example, a monoclonal antibody or an antigen binding fragment thereof, a polyclonal antibody or an antigen binding fragment thereof, or a biosynthetic antibody binding site that binds preferentially to a cell surface ligand disposed at elevated concentrations or densities in CNV. By way of example, the targeting moiety may be an antibody that binds specifically to the vascular endothelial growth factor receptor.

In another aspect, the invention provides a method of treating unwanted CNV in a mammal. The method comprises the steps of: (a) administering to the mammal, for example, a primate, and more preferably, a human, an apoptosis-modulating factor in an amount sufficient to permit an effective amount to localize in the CNV or tissue surrounding the CNV; (b) administering to the mammal an amount of photosensitizer sufficient to permit an effective amount of localize in the CNV; and (c) irradiating the CNV with laser light such that the light is absorbed by the photosensitizer so as to occlude the CNV. Cytotoxicity of the PDT can be enhanced and/or made more specific for CNV relative to a similar treatment lacking the apoptosis-modulating factor.

The apoptosis-modulating factor may be any molecule, for example, a protein, peptide, nucleic acid, peptidyl-nucleic acid, organic molecule or inorganic molecule, that enhances or stimulates apoptosis in cells or tissues of the CNV or that represses apoptosis in cells or tissues surrounding the CNV. In a preferred embodiment, the apoptosis-modulating factor is a peptide capable of inducing apoptosis in cells, for example, endothelial cells, present in CNV. The peptide may comprise, for example, an amino sequence comprising, in an N- to C-terminal direction, KLAK-LAKKLAKLAK (SEQ ID NO: 1) which is designed to be non-toxic outside cells, but which is toxic when internalized into target cells because it disrupts mitochondrial membranes. Furthermore, this peptide may be targeted towards endothelial cells by inclusion of a targeting amino acid sequence, for example, in an N- to C-terminal direction, ACDCRGDCFC (SEQ ID NO: 2), also known as RGD-4C.

The apoptosis-modulating factor may be co-administered simultaneously with the photosensitizer. However, in a preferred embodiment, the apoptosis-modulating factor is administered to the primate before administration of the photosensitizer and/or irradiation.

In all the foregoing methods, it is contemplated that any photosensitizer useful in PDT may be useful in the practice of the invention. Preferred photosensitizers include, for example, amino acid derivatives, azo dyes, xanthene derivatives, chlorins, tetrapyrrole derivatives, phthalocyanines, and assorted other photosensitizers. However, preferred photosensitizers, include, for example, lutetium texaphyrin, benzoporphyrin and derivatives thereof, and hematoporphyrin and derivatives thereof.

BRIEF DESCRIPTION OF THE DRAWINGS

The foregoing and other objects, features, and advantages of the present invention, as well as the invention itself, may be more fully understood from the following description of preferred embodiments, when read together with the accompanying drawings, in which.

DETAILED DESCRIPTION OF THE INVENTION

Figure 1A:
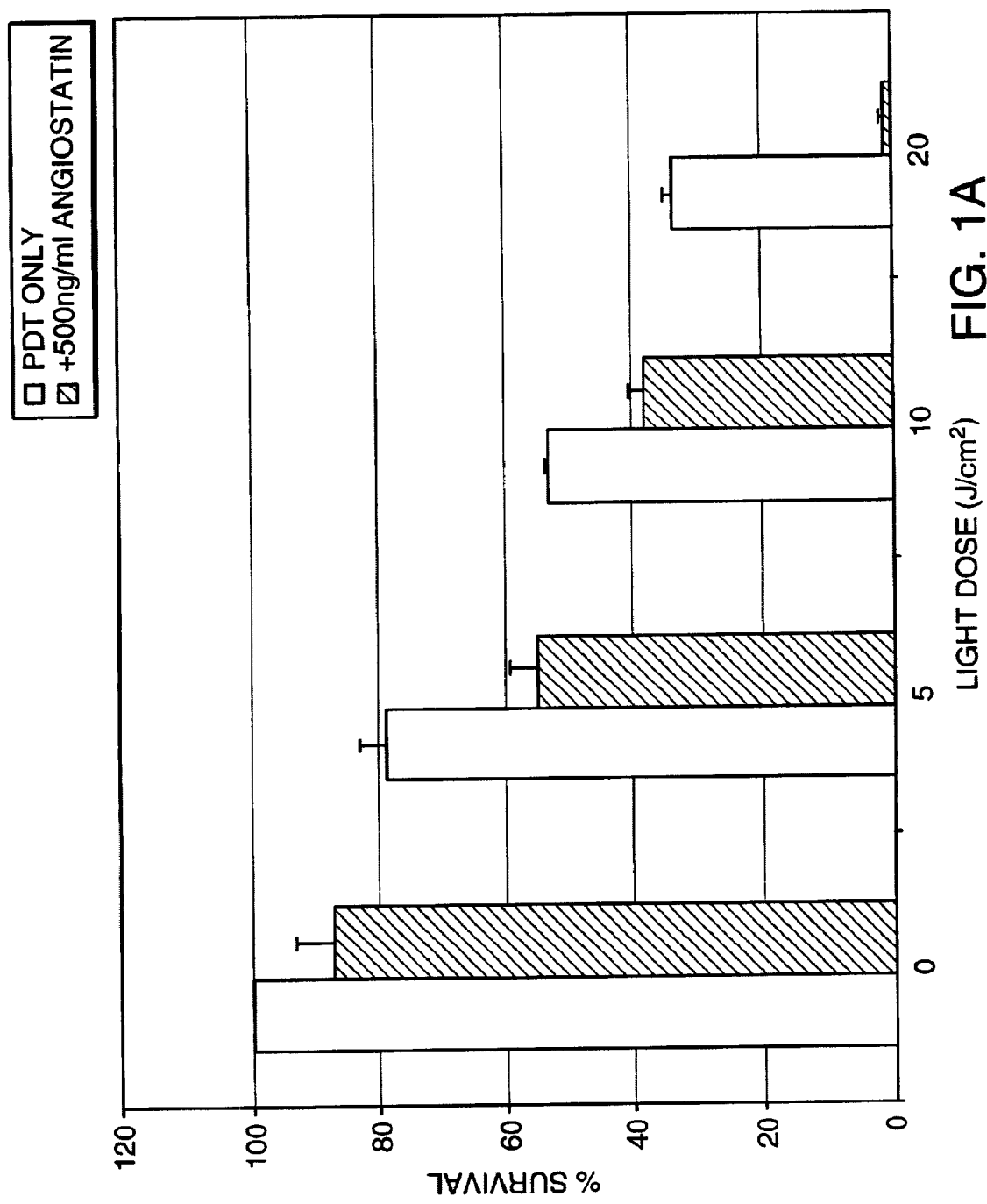
FIGS. 1A and 1B are bar charts showing the in vitro survival of bovine retinal capillary endothelial (BRCE) cells (FIG. 1A) and retinal pigment epithelial (RPE) cells (FIG. 1B) upon exposure to Lutetium Texaphyrin (Lu-Tex)/PDT in the presence or absence of angiostatin. Cells were plated and exposed to angiostatin 18 hours before Lu-Tex/PDT. The surviving fraction was measured using a 1-week proliferation assay. Data represent the mean of triplicate experiments ±SD.

The invention relates to an improved PDT-based method for treating ocular conditions characterized as having unwanted CNV. Such conditions include, for example, neovascular AMD, ocular histoplasmosis syndrome, pathologic myopia, angioid streaks, idiopathic disorders, choroiditis, choroidal rupture, overlying choroid nevi, and certain inflammatory diseases. The invention provides one or more of the following advantages: increased efficacy of treatment; increased selectivity for CNV; and reduced or delayed recurrence of the condition following PDT.

The method of the invention relates to a PDT-based method of treating unwanted target CNV. The method requires administration of a photosensitizer to a mammal in need of such treatment in an amount sufficient to permit an effective amount (i.e., an amount sufficient to facilitate PDT) of the photosensitizer to localize in the target CNV. After administration of the photosensitizer, the CNV then is irradiated with laser light under conditions such that the light is absorbed by the photosensitizer. The photosensitizer, when activated by the light, generates singlet oxygen and free radicals, for example, reactive oxygen species, that result in damage to surrounding tissue. For example, PDT-induced damage of endothelial cells results in platelet adhesion and degranulation, leading to stasis and aggregration of blood cells and vascular occlusion.

An increase in efficacy and/or selectivity of the PDT, and/or reduction or delay of recurrence of the CNV can be achieved by (i) administering an anti-angiogenic factor to the mammal prior to or concurrent with administration of the photosensitizer, (ii) using a photosensitizer with a targeting molecule that targets the photosensitizer to the CNV, (iii) administering an apoptosis-modulating factor to the mammal prior to or concurrent with administration of the photosensitizer, (iv) a combination of any two of the foregoing, for example, a combination of the anti-angiogenesis factor and the targeted photosensitizer, a combination of the anti-angiogenesis factor and the apoptosis modulating agent, or a combination of the targeted photosenitizer and the apoptosis modulating agent, or (v) a combination of all three of the foregoing.

It is contemplated that a variety of photosensitizers useful in PDT may be useful in the practice of the invention and include, for example, amino acid derivatives, azo dyes, xanthene derivatives, chlorins, tetrapyrrole derivatives, phthalocyanines, and assorted other photo sensitizers.

Amino acid derivatives include, for example, 5-aminolevulinic acid (Berg et al. (1997) PHOTOCHEM. PHOTOBIOL 65: 403–409; El-Far et al. (1985) CELL. BIOCHEM. FUNCTION 3, 115–119). Azo dyes, include, for example, Sudan I, Sudan II, Sudan III, Sudan IV, Sudan Black, Disperse Orange, Disperse Red, Oil Red O, Trypan Blue, Congo Red, β-carotene (Mosky et al. (1984) EXP. RES. 155, 389–396). Xanthene derivatives, include, for example, rose bengal.

Chlorins include, for example, lysyl chlorin p6 (Berg et al. (1997) supra) and etiobenzochlorin (Berg et al. (1997) supra), 5, 10, 15, 20-tetra (m-hydroxyphenyl) chlorin (M-THPC), N-aspartyl chlorin e6 (Dougherty et al. (1998) J. NATL. CANCER INST. 90: 889–905), and bacteriochlorin (Korbelik et al. (1992) J. PHOTOCHEM. PHOTOBIOL. 12: 107–119).

Tetrapyrrole derivatives include, for example, lutetium texaphrin (Lu-Tex, PCI-0123) (Dougherty et al. (1998) supra, Young et al. (1996) PHOTOCHEM. PHOTOBIOL. 63: 892–897); benzoporphyrin derivative (BPD) (U.S. Pat. Nos. 5,171,749, 5,214,036, 5,283,255, and 5,798,349, Jori et al. (1990) LASERS MED. SCI. 5, 115–120), benzoporphyrin derivative mono acid (BPD-MA) (U.S. Pat. Nos. 5,171,749, 5,214,036, 5,283,255, and 5,798,349, Berg et al. (1997) supra, Dougherty et al. (1998) supra), hematoporphyrin (Hp) (Jori et al. (1990) supra), hematoporphyrin derivatives (HpD) (Berg et al. (1997) supra, West et al. (1990) IN. J. RADIAT. BIOL. 58: 145–156), porfimer sodium or Photofrin (PHP) (Berg et al. (1997) supra), Photofrin II (PII) (He et al. (1994) PHOTOCHEM. PHOTOBIOL. 59: 468–473), protoporphyrin IX (PpIX) (Dougherty et al. (1998) supra, He et al. (1994) supra), meso-tetra (4-carboxyphenyl) porphine (TCPP) (Musser et al. (1982) RES. COMMUN. CHEM. PATHOL. PHARMACOL. 2, 251–259), meso-tetra (4-sulfonatophenyl) porphine (TSPP) (Musser et al. (1982) supra), uroporphyrin I (UROP-I) (El-Far et al. (1985) CELL. BIOCHEM. FUNCTION 3, 115–119), uroporphyrin III (UROP-III) (El-Far et al. (1985) supra), tin ethyl etiopurpurin (SnET2), (Dougherty et al. (1998) supra 90: 889–905) and 13, 17-bis[1-carboxypropionyl] carbamoylethyl-8-etheny-2-hydroxy-3-hydroxyiminoethyliden e-2, 7,12,18-tetranethyl 6 porphyrin sodium (ATX-S10(Na)) Mori et al. (2000) JPN. J. CANCER RES. 91:753–759, Obana et al (2000) ARCH. OPHTHALMOL. 118:650–658, Obana et al. (1999) LASERS SURG. MED. 24:209–222).

Phthalocyanines include, for example, chloroaluminum phthalocyanine (AlPcCl) (Rerko et al. (1992) PHOTOCHEM. PHOTOBIOL. 55, 75–80), aluminum phthalocyanine with 2–4 sulfonate groups (AlPcS$_{2-4}$) (Berg et al. (1997) supra, Glassberg et al. (1991) LASERS SURG. MED. 11, 432–439), chloroaluminum sulfonated phthalocyanine (CASPC) (Roberts et al. (1991) J. NATL. CANCER INST. 83, 18–32), phthalocyanine (PC) (Jori et al. (1990) supra), silicon phthalocyanine (Pc4) (He et al. (1998) PHOTOCHEM. PHOTOBIOL. 67: 720–728, Jori et al. (1990) supra), magnesium phthalocyanine (Mg$^{2+}$-PC) (Jori et al. (1990) supra), zinc phthalocyanine (ZnPC) (Berg et al. (1997) supra). Other photosensitizers include, for example, thionin, toluidine blue, neutral red and azure c.

However, preferred photosensitizers, include, for example, Lutetium Texaphyrin (Lu-Tex), a new generation photosensitizer currently in clinical trial for CNV because of its favorable clinical properties including absorption at about 730 nm permitting deep tissue penetration and rapid clearance which is available from Alcon Laboratories, Fort Worth, Tex. Other preferred photosensitizers, include benzoporhyrin and benzoporphyrin derivatives, for example, BPD-MA and BPD-DA, available from QLT Phototherapeutics, Inc., Vancouver, Canada.

The photosensitizer preferably is formulated into a delivery system that delivers high concentrations of the photosensitizer to the CNV. Such formulations may include, for example, the combination of a photosensitizer with a carrier that delivers higher concentrations of the photosensitizer to CNV and/or coupling the photosensitizer to a specific binding ligand that binds preferentially to a specific cell surface component of the CNV.

In one preferred embodiment, the photosensitizer can be combined with a lipid based carrier. For example, liposomal formulations have been found to be particularly effective at delivering the photosensitizer, green porphyrin, and more particularly BPD-MA to the low-density lipoprotein component of plasma, which in turn acts as a carrier to deliver the photosensitizer more effectively to the CNV. Increased numbers of LDL receptors have been shown to be associated with CNV, and by increasing the partitioning of the photosenstizer into the lipoprotein phase of the blood, it may be delivered more efficiently to the CNV. Certain photosensitizers, for example, green porphyrins, and in particular BPD-MA, interact strongly with lipoproteins. LDL itself can be used as a carrier, but LDL is considerably more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins formulated as lipocomplexes, including liposomes, are described, for example, in U.S. Pat. Nos. 5,214,036, 5,707,608 and 5,798,349. Liposomal formulations of green porphyrin can be obtained from QLT Phototherapeutics, Inc., Vancouver, Canada. It is contemplated that certain other photosensitizers may likewise be formulated with lipid carriers, for example, liposomes or LDL, to deliver the photosensitizer to CNV.

Furthermore, the photosensitizer can be coupled to a specific binding ligand that binds preferentially to a cell surface component of the CNV, for example, neovascular endothelial homing motif. It appears that a variety of cell surface ligands are expressed at higher levels in new blood vessels relative to other cells or tissues.

Endothelial cells in new blood vessels express several proteins that are absent or barely detectable in established blood vessels (Folkman (1995) NATURE MEDICINE 1:27–31), and include integrins (Brooks et al. (1994) SCIENCE 264: 569–571; Friedlander et al. (1995) SCIENCE 270: 1500–1502) and receptors for certain angiogenic factors like vascular endothelial growth factor (VEGF). In vivo selection of phage peptide libraries have also identified peptides expressed by the vasculature that are organ-specific, implying that many tissues have vascular "addresses" (Pasqualini et al. (1996) NATURE 380: 364–366). It is contemplated that a suitable targeting moiety can direct a photosensitizer to the CNV endothelium thereby increasing the efficacy and lowering the toxicity of PDT.

Several targeting molecules may be used to target photosensitizers to the neovascular endothelium. For example, α-v integrins, in particular α-v β3 and α-v β5, appear to be expressed in ocular neovascular tissue, in both clinical specimens and experimental models (Corjay et al. (1997) INVEST. OPHTHALMOL. VIS. SCI. 38, S965; Friedlander et al. (1995) supra). Accordingly, molecules that preferentially bind α-v integrins can be used to target the photosensitizer to CNV. For example, cyclic peptide antagonists of these integrins have been used to inhibit neovascularization in experimental models (Friedlander et al. (1996) PROC. NATL. ACAD. SCI. USA 93:9764–9769). A peptide motif having an amino acid sequence, in an N- to C-terminal direction, ACDCRGDCFC (SEQ ID NO: 2)—also know as RGD-4C—has been identified that selectively binds to human α-v integrins and accumulates in tumor neovasculature more effectively than other angiogenesis targeting peptides (Arap et al. (1998) NATURE 279:377–380; Ellerby et al. (1999) NATURE MEDICINE 5: 1032–1038). Angiostatin may also be used as a targeting molecule for the photosensitizer. Studies have shown, for example, that angiostatin binds specifically to ATP synthase disposed on the surface of human endothelial cells (Moser et al. (1999) PROC. NATL. ACAD. SCI. USA 96:2811–2816).

Another potential targeting molecule is an antibody for vascular endothelial growth factor receptor (VEGF-2R). Clinical and experimental evidence strongly supports a role for VEGF in ocular neovascularization, particularly ischemia-associated neovascularization (Adamis et aL (1996) ARCH. OPHTHALMOL. 114:66–71; Tolentino et al. (1996) ARCH. OPHTHALMOL. 114:964–970; Tolentino et al. (1996) OPHTHALMOLOGY 103:1820–1828). Antibodies to the VEGF receptor (VEGFR-2 also known as KDR) may also bind preferentially to neovascular endothelium. As used herein, the term "antibody" includes, for example, a monoclonal antibody or an antigen binding fragment thereof (for example, an Fv, Fab, Fab' or an (Fab')$_2$ molecule), a polyclonal antibody or an antigen binding fragment thereof, or a biosynthetic antibody binding site, for example, an sFv (U.S. Pat. Nos. 5,091,513; 5,132,405; 5,258,498; and 5,482,858) that binds specifically to a target ligand. As used herein, the terms binds "specifically" or "preferentially" are understood to mean that the targeting molecule, for example, the antibody, binds to the complementary or target ligand with a binding affinity of at least $10^5$, and more preferably $10^7$ $M^{-1}$.

The targeting molecule may be synthesized using methodologies known and used in the art. For example, proteins and peptides may be synthesized using conventional synthetic peptide chemistries or expressed as recombinant proteins or peptides in a recombinant expression system (see, for example, "Molecular Cloning" Sambrook et al. eds, Cold Spring Harbor Laboratories). Similarly, antibodies may be prepared and purified using conventional methodologies, for example, as described in "Practical Immunology", Butt, W. R. ed., 1984 Marcel Deckker, New York and "Antibodies, A Laboratory Approach" Harlow et al., eds. (1988), Cold Spring Harbor Press. Once created, the targeting agent may be coupled to the photosensitizer using standard coupling chemistries, using, for example, conventional cross linking reagents, for example, heterobifunctional cross linking reagents available, for example, from Pierce, Rockford, Ill.

Once formulated, the photosensitizer may be administered in any of a wide variety of ways, for example, orally, parenterally, or rectally. Parenteral administration, such as intravenous, intramuscular, or subcutaneous, is preferred. Intravenous injection is especially preferred. The dose of photosensitizer can vary widely depending on the tissue to be treated; the physical delivery system in which it is carried, such as in the form of liposomes; or whether it is coupled to a target-specific ligand, such as an antibody or an immunologically active fragment.

It should be noted that the various parameters used for effective, selective photodynamic therapy in the invention are interrelated. Therefore, the dose should also be adjusted with respect to other parameters, for example, fluence, irradiance, duration of the light used in PDT, and time interval between administration of the dose and the therapeutic irradiation. All of these parameters should be adjusted to produce significant damage to CNV without significant damage to the surrounding tissue.

Typically, the dose of photosensitizer used is within the range of from about 0.1 to about 20 mg/kg, preferably from about 0.15 to about 5.0 mg/kg, and even more preferably from about 0.25 to about 2.0 mg/kg. Furthermore, as the dosage of photosensitizer is reduced, for example, from about 2 to about 1 mg/kg in the case of green porphyrin or BPD-MA, the fluence required to close CNV may increase, for example, from about 50 to about 100 Joules/cm$^2$. Similar trends may be observed with the other photosensitizers discussed herein.

After the photosensitizer has been administered, the CNV is irradiated at a wavelength typically around the maximum absorbance of the photosensitizer, usually in the range from about 550 nm to about 750 nm. A wavelength in this range is especially preferred for enhanced penetration into bodily tissues. Preferred wavelengths used for certain photosensitizers include, for example, about 690 nm for benzoporphyrin derivative mono acid, about 630 nm for hematoporphyrin derivative, about 675 nm for chloro-aluminum sulfonated phthalocyanine, about 660 nm for tin ethyl etiopurpurin, about 730 nm for lutetium texaphyrin, about 670 nm for ATX-S10(NA), about 665 nm for N-aspartyl chlorin e6, and about 650 nm for 5, 10, 15, 20-tetra (m-hydroxyphenyl) chlorin.

As a result of being irradiated, the photosensitizer in its triplet state is thought to interact with oxygen and other compounds to form reactive intermediates, such as singlet oxygen and reactive oxygen species, which can disrupt cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to the endothelial cells, with subsequent platelet adhesion, degranulation, and thrombus formation.

The fluence during the irradiating treatment can vary widely, depending on the type of photosensitizer used, the type of tissue, the depth of target tissue, and the amount of overlying fluid or blood. Fluences preferably vary from about 10 to about 400 Joules/cm$^2$ and more preferably vary from about 50 to about 200 Joules/cm$^2$. The irradiance varies typically from about 50 mW/cm$^2$ to about 1800 mW/cm$^2$, more preferably from about 100 mW/cm$^2$ to about 900 mW/cm$^2$, and most preferably in the range from about 150 mW/cm$^2$ to about 600 mW/cm$^2$. It is contemplated that for many practical applications, the irradiance will be within the range of about 300 mW/cm$^2$ to about 900 mW/cm$^2$. However, the use of higher irradiances may be selected as effective and having the advantage of shortening treatment times.

The time of light irradiation after administration of the photosensitizer may be important as one way of maximizing the selectivity of the treatment, thus minimizing damage to structures other than the target tissues. The optimum time following photosensitizer administration until light treatment can vary widely depending on the mode of administration, the form of administration such as in the form of liposomes or as a complex with LDL, and the type of target tissue. For example, benzoporphyrin derivative typically becomes present within the target neovasculature within one minute post administration and persists for about fifty minutes, lutetium texaphyrin typically becomes present within the target neovasculature within one minute post administration and persists for about twenty minutes, N-aspartyl chlorin e6 typically becomes present within the target neovasculature within one minute post administration and persists for about twenty minutes, and rose bengal typically becomes present in the target vasculature within one minute post administration and persists for about ten minutes.

Effective vascular closure generally occurs at times in the range of about one minute to about three hours following administration of the photosensitizer. However, as with green porphyrins, it is undesirable to perform the PDT within the first five minutes following administration to prevent undue damage to retinal vessels still containing relatively high concentrations of photosensitizer.

The efficacy of PDT may be monitored using conventional methodologies, for example, via fundus photography or angiography. Closure can usually be observed angiographically by hypofluorescence in the treated areas in the early angiographic frames. During the later angiographic frames, a corona of hyperfluorescence may begin to appear which then fills the treated area, possibly representing leakage from the adjacent choriocapillaris through damaged retinal pigment epithelium in the treated area. Large retinal vessels in the treated area typically perfuse following photodynamic therapy.

Minimal retinal damage is generally found on histopathologic correlation and is dependent on the fluence and the time interval after irradiation that the photosensitizer is administered. It is contemplated that the choice of appropriate photosensitizer, dosage, mode of administration, formulation, timing post administration prior to irradiation, and irradiation parameters may be determined empirically.

It is contemplated that a variety of anti-angiogenic factors may be combined with PDT to treat unwanted CNV. The anti-angiogenesis factor can potentiate the cytotoxicity of the PDT thereby enhancing occlusion of the choroidal neovasculature. In addition, the anti-angiogenesis factor can enhance the selectivity of PDT, for example, by occluding the CNV while at the same sparing the surrounding blood vessels, for example, the retinal and large choroidal blood vessels and/or surrounding tissue, for example, the retinal epithelium. Furthermore, the anti-angiogenesis factor can be used to reduce or delay the recurrence of the condition.

The term "anti-angiogensis factor" is understood to mean any molecule, for example, a protein, peptide, nucleic acid (ribose nucleic acid (RNA) or deoxyribose nucleic acid (DNA)), peptidyl nucleic acid, organic compound or inorganic compound, that reduces or inhibits the formation of new blood vessels in a mammal. It is contemplated that useful angiogenesis inhibitors, if not already known, may be identified using a variety of assays well known and used in the art. Such assays include, for example, the bovine capillary endothelial cell proliferation assay, the chick chorioallantoic membrane (CAM) assay or the mouse corneal assay. However, the CAM assay is preferred (see, for example, O'Reilly et al. (1994) CELL 79: 315–328 and O'Reilly et al. (1997) CELL 88: 277–285). Briefly, embryos with intact yolks are removed from fertilized three day old white eggs and placed in a petri dish. After incubation at 37° C., 3% $CO_2$ for three days, a methylcellulose disk containing the putative angiogenesis inhibitor is applied to the chorioallantoic membrane of an individual embryo. After incubation for about 48 hours, the chorioallantoic membranes are observed under a microscope for evidence of zones of inhibition.

Numerous anti-angiogenesis factors are well known and thoroughly documented in the art (see, for example, PCT/US99/08335). Examples of anti-angiogenesis factors useful in the practice of the invention, include, for example, protein/peptide inhibitors of angiogenesis such as: angiostatin, a proteolytic fragment of plasminogen (O'Reilly et al. (1994) CELL 79: 315–328, and U.S. Pat. Nos. 5,733,876; 5,837,682; and 5,885,795) including full length amino acid sequences of angiostatin, bioactive fragments thereof, and analogs thereof; endostatin, a proteolytic fragment of collagen XVIII (O'Reilly et al. (1997) CELL 88: 277–285, Cirri et al. (1999) INT. BIOL. MARKER 14: 263–267, and U.S. Pat. No. 5,854,205) including full length amino acid sequences of endostatin, bioactive fragments thereof, and analogs thereof; peptides containing the RGD tripeptide sequence and capable of binding the $\alpha_v\beta_3$ integrin (Brooks et al. (1994) CELL 79: 1157–1164, Brooks et al. (1994) SCIENCE 264: 569–571); certain antibodies and antigen binding fragments thereof and peptides that bind preferentially to the $\alpha\beta_3$ integrin found on tumor vascular epithelial cells (Brooks et al, supra, Friedlander et al. (1996) PROC. NATL. ACAD. SCI. USA 93: 9764–9769); certain antibodies and antigen binding fragments thereof and peptides that bind preferentially to the epidermal growth factor receptor (Ciardello et al. (1996) J. NATL. CANCER INST. 88: 1770–1776, Ciardello et al. (2000) CLIN. CANCER RES. 6:3739–3747); antibodies, proteins, peptides and/or nucleic acids that bind preferentially to and neutralize vascular endothelial growth factor (Adamis et al. (1996) ARCH OPTHALMOL 114:66–71), antibodies, proteins, and/or peptides that bind preferentially to and neutralize vascular endothelial growth factor receptor; anti-fibroblast growth factor, anti-epidermal growth factor (Ciardiello et al. (2000) CLIN. CANCER RES. 6: 3739–3747) including full length amino acid sequences, bioactive fragments and analogs thereof, and pigment epithelium-derived growth factor (Dawson (1999) SCIENCE 2035: 245–248) including full length amino acid sequences, bioactive fragments and analogs thereof. Bioactive fragments refer to portions of the intact protein that have at least 30%, more preferably at least 70%, and most preferably at least 90% of the biological activity of the intact proteins. Analogs refer to species and allelic variants of the intact protein, or amino acid replacements, insertions or deletions thereof that have at least 30%, more preferably at least 70%, and most preferably 90% of the biological activity of the intact protein.

Other angiogenesis inhibitors include, for example: COX-2 selective inhibitors (Masferrer et al. (1998) PROC. AMER. ASSOC. CANCER RES. 39: 271; Ershov et al. (1999) J. NEUROSCI. RES. 15: 254–261; Masferrer et al. (2000) CURR. MED. CHEM. 7: 1163–1170); tyrosine kinase inhibitors, for example, PD 173074 (Dimitroff et al. (1999) INVEST. NEW DRUGS 17: 121–135), halofuginone (Abramovitch et al. (1999) NEOPLASIA 1: 321–329; Elkin et al. (1999) CANCER RES. 5: 1982–1988), AGM-1470 (Brem et al. (1993) J. PED. SURGERY 28: 1253–1257), angiogenic steroids, for example, hydrocortisone and anecortave acetate (Penn et al. (2000) INVEST. OPHTHALMOL. VIS. SCI. 42: 283–290), thrombospondin-1 (Shafiee et al. (2000) INVEST. OPHTHALMOL. VIS. SCI. 8: 2378–2388; Nor et al. (2000) J. VASC. RES. 37: 09–218), UCN-01 (Kruger et al. (1998–1999) INVASION METASTASIS 18: 209–218), CM101 (Sundell et al. (1997) CLIN. CANCER RES. 3: 365–372); fumagillin and analogues such as AGM-1470 (Ingber et aL (1990) NATURE 348: 555–557), and other small molecules such as thalidomide (D'Amato et al. (1994) PROC. NATL. ACAD. SCI. USA 91: 4082–4085).

Several cytokines including bioactive fragments thereof and analogs thereof have also been reported to have anti-angiogenic activity and thus can be useful in the practice of the invention. Examples include, for example, IL-12, which reportedly works through an IFN-γ-dependent mechanism (Voest et al. (1995) J. NATL. CANC. INST. 87: 581–586); IFN-α, which has been shown to be anti-angiogenic alone or in combination with other inhibitors (Brem et al. (1993) J. PEDIATR. SURG. 28: 1253–1257). Furthermore, the interferons IFN-α, IFN-β and IFN-γ reportedly have immunological effects, as well as anti-angiogenic properties, that are independent of their anti-viral activities. However, preferred anti-angiogenic factors include endostatin and angiostatin.

The anti-angiogenesis factor may be synthesized using methodologies known and used in the art. For example, proteins and peptides may be synthesized and purified using conventional synthetic peptide chemistries and purification protocols, or expressed as recombinant proteins or peptides in a recombinant expression system (see, for example, "Molecular Cloning" Sambrook et al. eds, Cold Spring Harbor Laboratories). Similarly, antibodies may be prepared and purified using conventional methodologies, for example, as described in "Practical Immunology", Butt, W. R. ed., 1984 Marcel Deckker, New York and "Antibodies, A Laboratory Approach" Harlow et al., eds. (1988), Cold Spring Harbor Press.

To the extent that the anti-angiogenesis factor is a nucleic acid or peptidyl nucleic acid, such compounds may be synthesized by any of the known chemical oligonucleotide and peptidyl nucleic acid synthesis methodologies known in the art (see, for example, PCT/EP92/20702 and PCT/US94/013523) and used in antisense therapy. Anti-sense oligonucleotide and peptidyl nucleic acid sequences, usually 10 to 100 and more preferably 15 to 50 units in length, are capable of hybridizing to a gene and/or mRNA transcript and, therefore, may be used to inhibit transcription and/or translation of a target protein. It is appreciated, however, that oligoribonucleotide sequences generally are more susceptible to enzymatic attack by ribonucleases than are deoxyribonucleotide sequences. Hence, oligodeoxyribonucleotides are preferred over oligoribonucleotides for in vivo use. In the case of nucleotide sequences, phosphodiester linkages may be replaced by thioester linkages making the resulting molecules more resistant to nuclease degradation. Furthermore, it is appreciated that the peptidyl nucleic acid sequences, unlike regular nucleic acid sequences, are not susceptible to nuclease degradation and, therefore, are likely to have greater longevity in vivo. Furthermore, it has been found that peptidyl nucleic acid sequences bind complementary single stranded DNA and RNA strands more strongly than corresponding DNA sequences (PCT/EP92/20702). Furthermore, to the extent that the anti-angiogenesis factor is an organic or inorganic compound, such compounds may be synthesized, extracted and/or purified by standard procedures known in the art.

The type and amount of anti-angiogenesis factor to be administered may depend upon the PDT and cell type to be treated. It is contemplated, however, that optimal anti-angiogenesis factors, modes of administration and dosages may be determined empirically. The anti-angiogensis factor may be administered in a pharmaceutically acceptable carrier or vehicle so that administration does not otherwise adversely affect the recipient's electrolyte and/or volume balance. The carrier may comprise, for example, physiologic saline.

Protein, peptide or nucleic acid based angiogenesis inhibitors can be administered at doses ranging, for example, from about 0.001 to about 500 mg/kg, more preferably from about 0.01 to about 250 mg/kg, and most preferably from about 0.1 to about 100 mg/kg. For example, antibodies that bind vascular epithelial growth factor may be administered intravenously at doses ranging from about 0.1 to about 5 mg/kg once every two to four weeks. Endostatin, for example, may be administered intravenously on a daily basis at dosages ranging from about 1 to about 50 mg/kg per day. With regard to intravitreal administration, the anti-angiogenesis factor, for example, antibodies that bind vascular epithelial growth factor, typically is administered periodically as boluses at dosages ranging from about 10 µg to about 5 mg/eye and more preferably from about 100 µg to about 2 mg/eye.

The anti-angiogenesis factor preferably is administered to the mammal prior to PDT. Accordingly, it is preferable to administer the anti-angiogenesis factor prior to administration of the photosensitizer. The anti-angiogenesis factor, like the photosensitizer, may be administered in any one of a wide variety of ways, for example, orally, parenterally, or rectally. However, parenteral administration, such as intravenous, intramuscular, subcutaneous, and intravitreal, is preferred. Administration may be provided as a periodic bolus (for example, intravenously or intavitreally) or as continuous infusion from an internal reservoir (for example, from a bioerodable implant disposed at an intra- or extraocular location) or from an external reservoir (for example, from an intravenous bag). The anti-angiogenesis factor may be administered locally, for example, by continuous release from a sustained release drug delivery device immobilized to an inner wall of the eye or via targeted trans-scleral controlled release into the choroid (see, PCT/US00/00207).

The present invention, therefore, includes the use of an anti-angiogenesis factor in the preparation of a medicament for treating, preferably by a PDT-based method, an ocular condition, that preferably is associated with choriodal neovasculature. The anti-angiogenesis factor may be provided in a kit which optionally may comprise a package insert with instructions for how to treat such a condition. A composition comprising both a photosensitizer and an anti-angiogenesis factor may be provided for use in the present invention. The composition may comprise a pharmaceutically acceptable carrier or excipient. Thus, the present invention includes a pharmaceutically acceptable composition comprising a photosensitizer and an anti-angiogenesis factor; as well as the composition for use in medicine. More preferably, however, the invention is for use in combination therapy, whereby an anti-angiogenesis factor and a photosensitizer are administered separately. Preferably the anti-angiogenesis factor is administered prior to administration of the photosensitizer. Instructions for such administration may be provided with the anti-angiogenesis factor and/or with the photosensitizer. If desired, the anti-angiogenesis factor and photosensitizer may be provided together in a kit, optionally including a package insert with instructions for use. The anti-angiogenesis factor and photosensitizer preferably are provided in separate containers. For each administration, the anti-angiogenesis factor and/or photosensitizer may be provided in unit-dosage or multiple-dosage form. Preferred dosages of photosensitizer and anti-angiogenic factor, however, are as described above.

In addition, the efficacy and selectivity of the PDT method may be enhanced by combining the PDT with an apoptosis-modulating factor. An apoptosis-modulating factor can be any factor, for example, a protein (for example a growth factor or antibody), peptide, nucleic acid (for example, an antisense oligonucleotide), peptidyl nucleic acid (for example, an antisense molecule), organic molecule or inorganic molecule, that induces or represses apoptosis in a particular cell type. For example, it may be advantageous to prime the apoptotic machinery of CNV endothelial cells with an inducer of apoptosis prior to PDT so as to increase their sensitivity to PDT. Endothelial cells primed in this manner are contemplated to be more susceptible to PDT. This approach may also reduce the light dose (fluence) required to achieve CNV closure and thereby decreasing the level of damage on surrounding cells such as RPE. Alternatively, the cells outside the CNV may be primed with an a repressor of apoptosis so as to decrease their sensitivity to PDT. In this approach, the PDT at a particular fluence can become more selective for CNV.

Apoptosis involves the activation of a genetically determined cell suicide program that results in a morphologically distinct form of cell death characterized by cell shrinkage, nuclear condensation, DNA fragmentation, membrane reorganization and blebbing (Kerr et al. (1972) BR. J. CANCER 26: 239–257). At the core of this process lies a conserved set of proenzymes, called caspases, and two important members of this family are caspases 3 and 7 (Nicholson et al. (1997) TIBS 22:299–306). Monitoring their activity can be used to assess on-going apoptosis.

It has been suggested that apoptosis is associated with the generation of reactive oxygen species, and that the product of the $Bcl_{-2}$ gene protects cells against apoptosis by inhibiting the generation or the action of the reactive oxygen species (Hockenbery et al. (1993) CELL 75: 241–251, Kane et al. (1993) SCIENCE 262: 1274–1277, Veis et al. (1993) CELL 75: 229–240, Virgili et al. (1998) FREE RADICALS BIOL. MED. 24: 93–101). $Bcl_{-2}$ belongs to a growing family of apoptosis regulatory gene products, which may either be death antagonists ($Bcl_{-2}$, $Bcl-x_L$. . . ) or death agonists (Bax, Bak . . . ) (Kroemer et al. (1997) NAT. MED. 3: 614–620). Control of cell death appears to be regulated by these interactions and by constitutive activities of the various family members (Hockenbery et al. (1993) CELL 75: 241–251). Several apoptotic pathways may coexist in mammalian cells that are preferentially activated in a stimulus-, stage-, context-specific and cell-type manner (Hakem et al. (1998) CELL 94: 339–352).

The apoptosis-inducing factor preferably is a protein or peptide capable of inducing apoptosis in cells, for example, endothelial cells, disposed in the CNV. One apoptosis inducing peptide comprises an amino sequence having, in an N- to C-terminal direction, KLAKLAKKLAKLAK (SEQ ID NO: 1). This peptide reportedly is non-toxic outside cells, but become toxic when internalized into targeted cells by disrupting mitochondrial membranes (Ellerby et al. (1999) supra). This sequence may be coupled, either by means of a crosslinking agent or a peptide bond, to a targeting domain, for example, the amino acid sequence known as RGD-4C (Ellerby et al. (1999) supra) that reportedly can direct the apoptosis-inducing peptide to endothelial cells. Other apoptosis-inducing factors include, for example, constatin (Kamphaus et al. (2000) J. BIOL. CHEM. 14: 1209–1215), tissue necrosis factor aX (Lucas et al. (1998) BLOOD 92: 4730–4741) including bioactive fragments and analogs thereof, cycloheximide (O'Connor et al. (2000) AM. J. PATHOL. 156: 393–398), tunicamycin (Martinez et al. (2000) ADV. EXP. MED. BIOL. 476: 197–208), adenosine (Harrington et al. (2000) AM. J. PHYSIOL. LUNG CELL MOL. PHYSIOL. 279: 733–742). Furthermore, other apoptosis-inducing factors may include, for example, anti-sense nucleic acid or peptidyl nucleic acid sequences that reduce or turn off the expression of one or more of the death antagonists, for example ($Bcl_{-2}$, $Bcl-x_L$). Antisense nucleotides directed against $Bcl_{-2}$ have been shown to reduce the expression of $Bcl_{-2}$ protein in certain lines together with increased phototoxicity and susceptibility to apoptosis during PDT (Zhang et al. (1999) PHOTOCHEM PHOTOBIOL 69: 582–586). Furthermore, an 18mer phosphorothiate oligonucleotide complementary to the first six codons of the Bcl-$_2$ open reading frame, and known as G3139, is being tested in humans as a treatment for non-Hodgkins' lymphoma.

Apoptosis-repressing factors include, survivin including bioactive fragments and analogs thereof (Papapetropoulos et al. (2000) J. BIOL. CHEM. 275: 9102–9105), CD39 (Goepfert et al. (2000) MOL. MED. 6: 591–603), BDNF (Caffe et al. (2001) INVEST. OPHTHALMOL. VIS. SCI. 42: 275–82), FGF2 (Bryckaert et al. (1999) ONCOGENE 18: 7584–7593), Caspase inhibitors (Ekert et al. (1999) CELL DEATH DIFFER 6: 1081–1068) and pigment epithelium-derived growth factor including bioactive fragments and analogs thereof. Furthermore, other apoptosis-repressing factors may include, for example, anti-sense nucleic acid or peptidyl nucleic acid sequences that reduce or turn off the expression of one or more of the death agonists, for example (Bax, Bak).

To the extent that the apoptosis-modulating factor is a protein or peptide, nucleic acid, peptidyl nucleic acid, organic or inorganic compound, it may be synthesized and purified by one or more the methodologies described relating to the synthesis of the anti-angiogenesis factor.

The type and amount of apoptosis-modulating factor to be administered may depend upon the PDT and cell type to be treated. It is contemplated, however, that optimal apoptosis-modulating factors, modes of administration and dosages may be determined empirically. The apoptosis modulating factor may be administered in a pharmaceutically acceptable carrier or vehicle so that administration does not otherwise adversely affect the recipient's electrolyte and/or volume balance. The carrier may comprise, for example, physiologic saline.

Protein, peptide or nucleic acid based apoptosis modulators can be administered at doses ranging, for example, from about 0.001 to about 500 mg/kg, more preferably from about 0.01 to about 250 mg/kg, and most preferably from about 0.1 to about 100 mg/kg. For example, nucleic acid-based apoptosis inducers, for example, G318, may be administered at doses ranging from about 1 to about 20 mg/kg daily. Furthermore, antibodies may be administered intravenously at doses ranging from about 0.1 to about 5 mg/kg once every two to four weeks. With regard to intravitreal administration, the apoptosis modulators, for example, antibodies, may be administered periodically as boluses a dosages ranging from about 10 µg to about 5 mg/eye and more preferably from about 100 µg to about 2 mg/eye.

The apoptosis-modulating factor preferably is administered to the mammal prior to PDT. Accordingly, it is preferable to administer the apoptosis-modulating factor prior to administration of the photosensitizer. The apoptosis-modulating factor, like the photosensitizer and anti-angiogenesis factor, may be administered in any one of a wide variety of ways, for example, orally, parenterally, or rectally. However, parenteral administration, such as intravenous, intramuscular, subcutaneous, and intravitreal is preferred. Administration may be provided as a periodic bolus (for example, intravenously or intravitreally) or by continuous infusion from an internal reservoir (for example, bioerodable implant disposed at an intra- or extra-ocular location) or an external reservoir (for example, and intravenous bag). The apoptosis modulating factor may be administered locally, for example, by continuous release from a sustained release drug delivery device immobilized to an inner wall of the eye or via targeted trans-scleral controlled release into the choroid (see, PCT/US00/00207).

Although the foregoing methods and compositions of the invention may be useful in treated unwanted choroidal neovasculature and thereby ameliorating the symptoms of ocular disorders including, for example, AMD, ocular histoplasmosis syndrome, pathologic myopia, angioid streaks, idiopathic disorders, choroiditis, choroidal rupture, overlying choroid nevi, and inflammatory diseases, it is contemplated that the same methods and compositions may also be useful in treating other forms of ocular neovasculature. More specifically, the methods and compositions of the invention may likewise be useful at treating and removing or reducing corneal neovasculature, iris neovasculature, retinal neovasculature, retinal angiomas and choroidal hemangiomas.

The invention is illustrated further by reference to the following non-limiting examples.

EXAMPLE 1

Anti-Angiogenesis Factor Potentiates the Effect of PDT on Endothelial Cells

Experiments were performed to determine whether the cytotoxicity resulting from PDT can be potentiated by the addition of an anti-angiogenesis factor. Cells of interest were treated by PDT either alone or in combination with an anti-angiogenesis factor and the effect on cytotoxicity of the PDT assessed via a cell proliferation assay.

Bovine retinal capillary endothelial (BRCE) cells (from Patricia A. D'Amore, Schepens Eye Research Institute, Boston, Mass.) and Human retinal pigment epithelial (RPE) cells (from Anthony P. Adamis, Massachusetts Eye & Ear Infirmary, Boston, Mass.) were grown at 37° C., 5% $CO_2$ in Dulbecco's modified Eagle's medium (DMEM; Sigma, St. Louis, Mo.), 5% heat-inactivated fetal bovine serum (FBS, Gibco, Grand Island, N.Y.), supplemented with L-glutamine, penicillin, and streptomycin (Gibco Grand Island, N.Y.). Lutetium Texaphyrin (Lu-Tex) was obtained from Alcon Laboratories, Inc. (Fort Worth, Tex.) as a stock solution of 2 mg/ml, stable in the dark at 4° C., and used in accordance with the manufacturer's guidelines.

Cell survival was measured using a cell proliferation assay. Briefly, BRCE or RPE cells were plated at a density of $10^5$ cells in DMEM with 5% FBS and incubated at 37° C. in 5% $CO_2$. After eighteen hours, and if desired, recombinant human angiostatin (Calbiochem, La Jolla, Calif.) was added at a concentration of 500 ng/ml. Eighteen hours later, the medium was removed and replaced by 3 µg/ml Lu-Tex in complete media. Thirty minutes later, the cultures were exposed to timed irradiation using an argon/dye Photocoagulator at 732 nm and laser delivery system (model 920, Coherent Inc., Palo Alto, Calif.). Irradiance was delivered at a rate of 10 mw/cm$^2$ to give a total dose of 5 to 20 J/cm$^2$, and irradiation time ranged from 7 to 28 minutes. After irradiation, the medium was removed and replaced with complete medium. Cultures were returned to the incubator for 7 days, after which cells were dispersed in trypsin, counted in a masked fashion, and the surviving fraction determined. The results, reported as the mean of triplicate ± SD, are summarized in Table 1. Cultures were photographed at various times following Lu-Tex/PDT using a 16×-0.32 numeric aperture on a phase contrast inverted microscope (Diaphot, Nikon, Melville, N.Y.).

TABLE 1

Summary of Cellular Survival (%) as a Function of Treatment*

| Cell Line | Lu-Tex/PDT | Angiostatin | Angiostatin followed by Lu-Tex/PDT | Lu-Tex/PDT followed by Angiostatin |
|---|---|---|---|---|
| BRCE | 79.13 ± 4.05 (5J/cm$^2$) | 87.39 ± 5.76 | 55.22 ± 3.65 | 77.61 ± 3.52 |
|  | 53.17 ± 0.32 (10J/cm$^2$) |  | 38.11 ± 2.50 | 67.16 ± 3.20 |
|  | 33.34 ± 2.26 (20J/cm$^2$) |  | 0.90 ± 0.32 | 32.97 ± 2.20 |
| RPE | 94.55 ± 1.60 (5J/cm$^2$) | 99.09 ± 0.8 | 91.84 ± 7.97 |  |
|  | 59.59 ± 3.56 (10J/cm$^2$) |  | 56.84 ± 6.61 |  |
|  | 53.47 ± 3.18 (20J/cm$^2$) |  | 45.83 ± 5.51 |  |

*The interactive in vitro anti-endothelial effect of combined treatment with angiostatin and Lu-Tex/PDT are greater than additive when compared with the sum of expected effects of each treatment alone. The potentiation of Lu-Tex/PDT effect on BRCE was effective with pre-exposure to angiostatin only. No effect of angiostatin was observed on RPE. Data are mean % cellular survival ± SD.

In order to assess the effect of combining angiostatin to Lu-Tex/PDT on BRCE cell survival, cells were pre-treated for 18 hours with 500 ng/ml angiostatin after which they were treated with Lu-Tex/PDT at various fluences. Cellular survival was measured by the 1-week cellular proliferation assay. When exposed to angiostatin alone, the proliferation assay demonstrated a 12.61% killing of BRCE cells at the angiostatin dose used (Table 1). Pre-exposing BRCE cells to angiostatin did not appear to interfere with the subsequent cellular uptake of Lu-Tex. More importantly, the results showed a synergistic cytotoxic effect of angiostatin and Lu-Tex/PDT on BRCE cells at all fluences used (5, 10 and 20 J/cm$^2$), consistently exceeding the cytotoxicity resulting from Lu-Tex/PDT alone, angiostatin alone or the arithmetic sum of their respective toxicity's (Table 1, FIG. 1A). Controls consisted of cells exposed to light only because no dark toxicity was observed at the concentration of Lu-Tex used. Furthermore, it was observed that angiostatin was not effective in potentiating the effect of Lu-Tex/PDT if delivered after PDT.

Figure 1B:
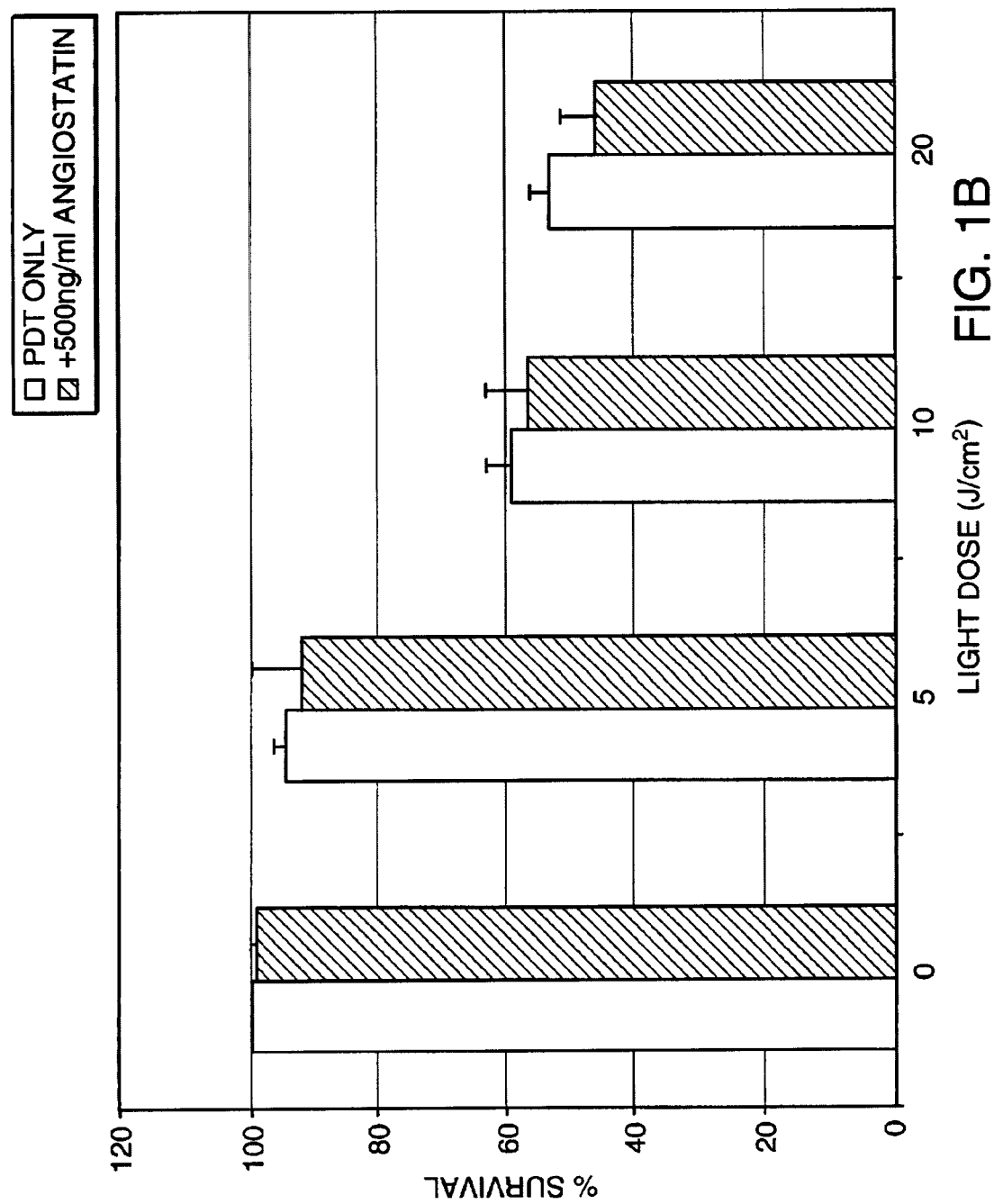

In contrast to the results obtained with BRCE cells, no cytotoxicity was observed when human RPE cells were treated with human angiostatin, and no interactive killing was observed following exposure to angiostatin and Lu-Tex/PDT (FIG. 1B, Table 1). When combined with angiostatin, Lu-Tex/PDT had a lethal dose ($LD_{100}$) of 20 J/cm$^2$ for BRCE cells whereas Lu-Tex/PDT alone required 40 J/cm$^2$ to achieve the same effect on BRCE cells. Previous studies showed that at fluences of 20 and 40 J/cm$^2$, RPE cell survival is about 43% and 21%, respectively.

The data show a specific anti-proliferative effect of angiostatin on BRCE cells as demonstrated by the reduction in cell number in a 1-week proliferation assay. In contrast, no effect of angiostatin was observed on RPE cells. Accordingly, BRCE cells appear to be another endothelial cell line, along with bovine adrenal cortex-microvascular cells, bovine adrenal cortex capillary cells, bovine aortic cells, human umbilical vein cells and human dermal microvascular endothelium cells (Mauceri et al. (1998) NATURE 394: 287–291, Lucas et al. (1998) BLOOD 92: 4730–41), that is specifically targeted by angiostatin. In this study, BRCE cells were used a representative capillary endothelial line of the posterior segment to test the anti-angiogenic effect of angiostatin. The finding that angiostatin induces apoptosis in BRCE cells suggests that cell death might contribute to the overall reduction of cell number. However, little is known concerning the exact anti-angiogenic mechanism of angiostatin (Lucas et al. (1998) BLOOD 92: 4730–4741).

In summary, the studies show that Lu-Tex/PDT and angiostatin have combined cytotoxic effects on retinal capillary endothelial cells, but not on pigment epithelial cells. However, when angiostatin was administered after PDT, the combination did not potentiate the effects of PDT. In the combination of angiostatin before Lu-Tex/PDT, a fluence of 20 J/cm$^2$ sufficed to achieve nearly 100% mortality of BRCE. In the absence of angiostatin, a light dose of 40 J/cm$^2$ was required to achieve this level of cytotoxicity. At the light dose of 20 J/cm$^2$, RPE cell survival post-PDT was improved by 20%. The results thus support the potential of combining angiostatin with Lu-Tex/PDT to improve CNV eradication and to decrease deleterious effects on the RPE.

EXAMPLE 2

Cellular Morphology Following PDT with Anti-Angiogenic Factor

Experiments were performed to establish how PDT effects the cellular morphology of BRCE and RPE cells. The cells were treated and exposed to PDT either alone or in combination with angiostatin as described in Example 1. Although cells appeared severely damaged immediately after PDT, subsequent recovery occurred in certain circumstances. One week after PDT, some cells disappeared while those that remained regained their spindle shape and their ability to attach.

In BRCE cells that were first primed with angiostatin followed by PDT, widespread and massive cell death was observed at one week. Only remnants of cells and densely refractive bodies of dying cells were observed floating in the medium. Particles were recovered and placed in fresh complete media but none showed any sign of reattachment or proliferation onto a new dish. The combination of angiostatin and Lu-Tex/PDT, therefore, appears to be lethal to BRCE under the conditions used.

Control BRCE cells and RPE cells which were treated with angiostatin alone for 18 hours continued to proliferate and reached confluence. No additive effect of angiostatin to Lu-Tex/PDT was observed in RPE cells. RPE cells subjected to Lu-Tex/PDT alone or with angiostatin appeared unchanged as evidenced by their morphology.

EXAMPLE 3

Caspase 3-Like (DEVD-ase) Activation in BRCE and RPE Following PDT

In order to investigate the role of apoptosis in Lu-Tex/PDT mediated cell death in BRCE and RPE, the activation of Caspase 3-like (DEVD-ase) protease, a hallmark of apoptosis (Nicholson (1997) TIBS 22: 299–306), was monitored. The kinetics of activation were measured spectrofluorometrically by assaying the hydrolysis of a substrate that can be cleaved only by the caspase 3-like protease family members.

Various times after Lu-Tex/PDT, 10$^6$ cells were collected by centrifugation, and the washed cell pellet resuspended in 500 µl of ice-cold lysis buffer (pH 7.5) containing 10 mM Tris, 130 mM NaCl, 1% Triton X-100, 10 mM NaF, 10 mM NaPi, 10 mM NaPPi, 16 µg/ml benzamidine, 10 µg/ml phenanthroline, 10 µg/ml aprotinin, 10 µg/ml leupeptin, 10 µg/ml pepstatin and 4 mM 4(2-aminoethyl)-benzene-sulfanyl fluoride hydrochloride (AEBSF). Cellular lysates were stored in aliquots at −84° C. for later protease activity assay or Western blot analysis. A protein assay (Coomassie Plus protein assay (Pierce, Rockford, Ill.) with a bovine serum albumin (BSA) standard was used to assay protein concentration in cell extract.

In order to measure protease activity, aliquots containing 50 1 µg of cellular protein were incubated with 14 µM (final concentration N-acetyl (Asp-Glu-Val-Asp (SEQ. ID NO: 3)-(7-amino-4-trifluoromethly coumarin) (Ac-DEVD-AFC); (Pharmingen San Diego, Calif.) in 1 ml protease assay buffer pH 7.2 (20 mM piperazine-N-N$^1$-bis (2-ethanesulfuric acid) (PIPES), 100 mM NaCl, 10 mM dithiothreitol (DTT), 1 mM EDTA, 0.1%(w/v) 3-[(3-Cholamidopropyl) dimethyl ammonio]-1-propane sulfonate (CHAPS), and 10% sucrose) at 37° C. for 1 hour. Fluorescence was measured using a Perkin-Elmer MPF-44A spectrofluorometer ($\lambda_{excitation}$, 400 nm; $\lambda_{emission}$ 505 nm). Cellular protein served as the blank. Results were compared with a standard curve constructed with AFC (Sigma, St. Louis, Mo.) and are shown in FIG. 2.

Figure 2A:
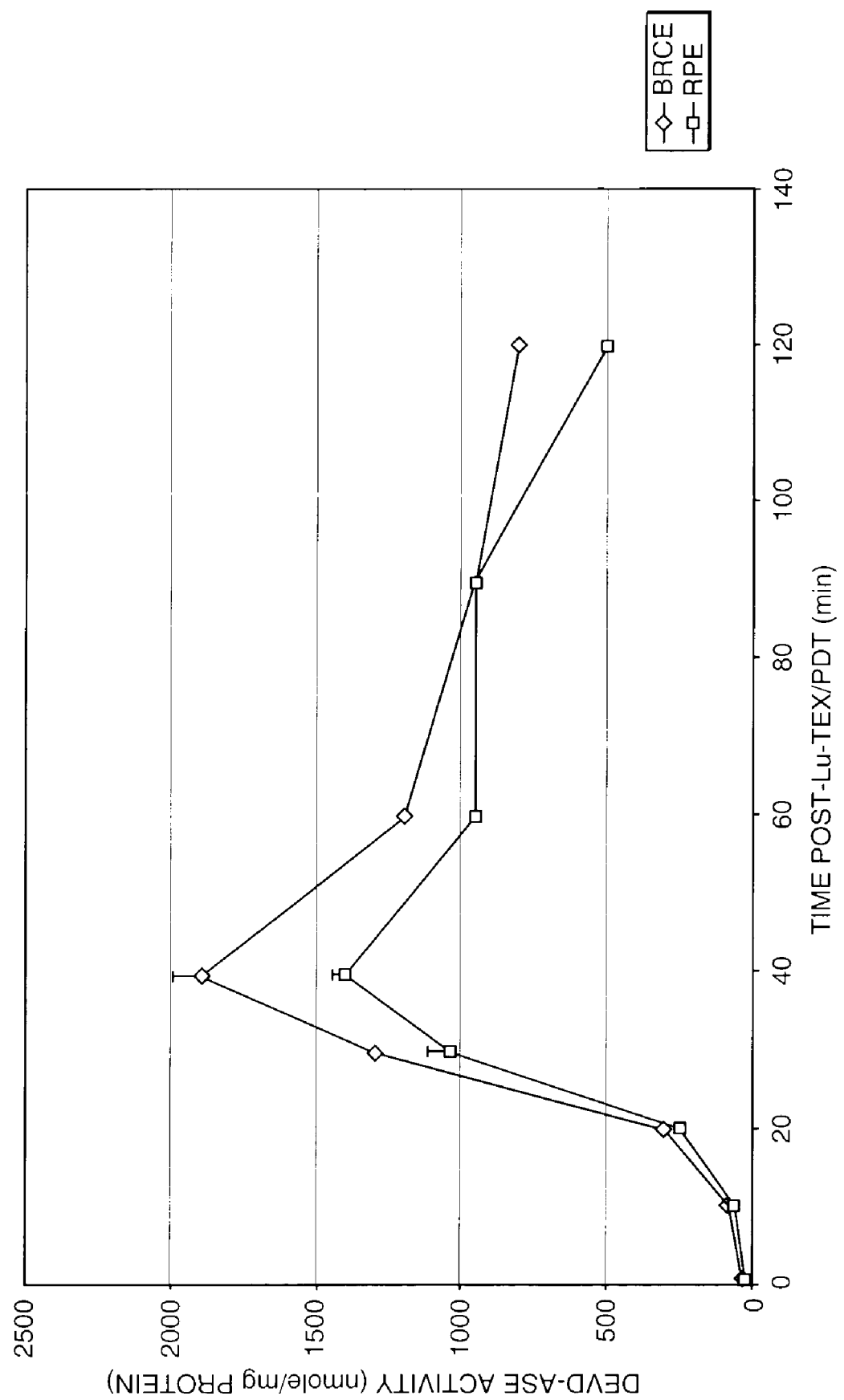
FIGS. 2A–2C are graphs showing the kinetics of Caspase 3-like activation following Lu-Tex/PDT in BRCE (diamonds) and RPE (squares). BRCE and RPE cells were exposed to Lu-Tex/PDT at fluences of 10 J/cm$^2$ (FIG. 2A), 20 J/cm$^2$ (FIG. 2B) and 40 J/cm$^2$ (FIG. 2C). At the indicated times thereafter, cells were collected and lysed. Aliquots (50 µg of protein) were incubated with Ac-DEVD-AFC at 37° C. for 30 min. The amount of fluorochrome released was determined by comparison to a standard curve in lysis buffer and the data represent the mean of three independent experiments.
Figure 2B:
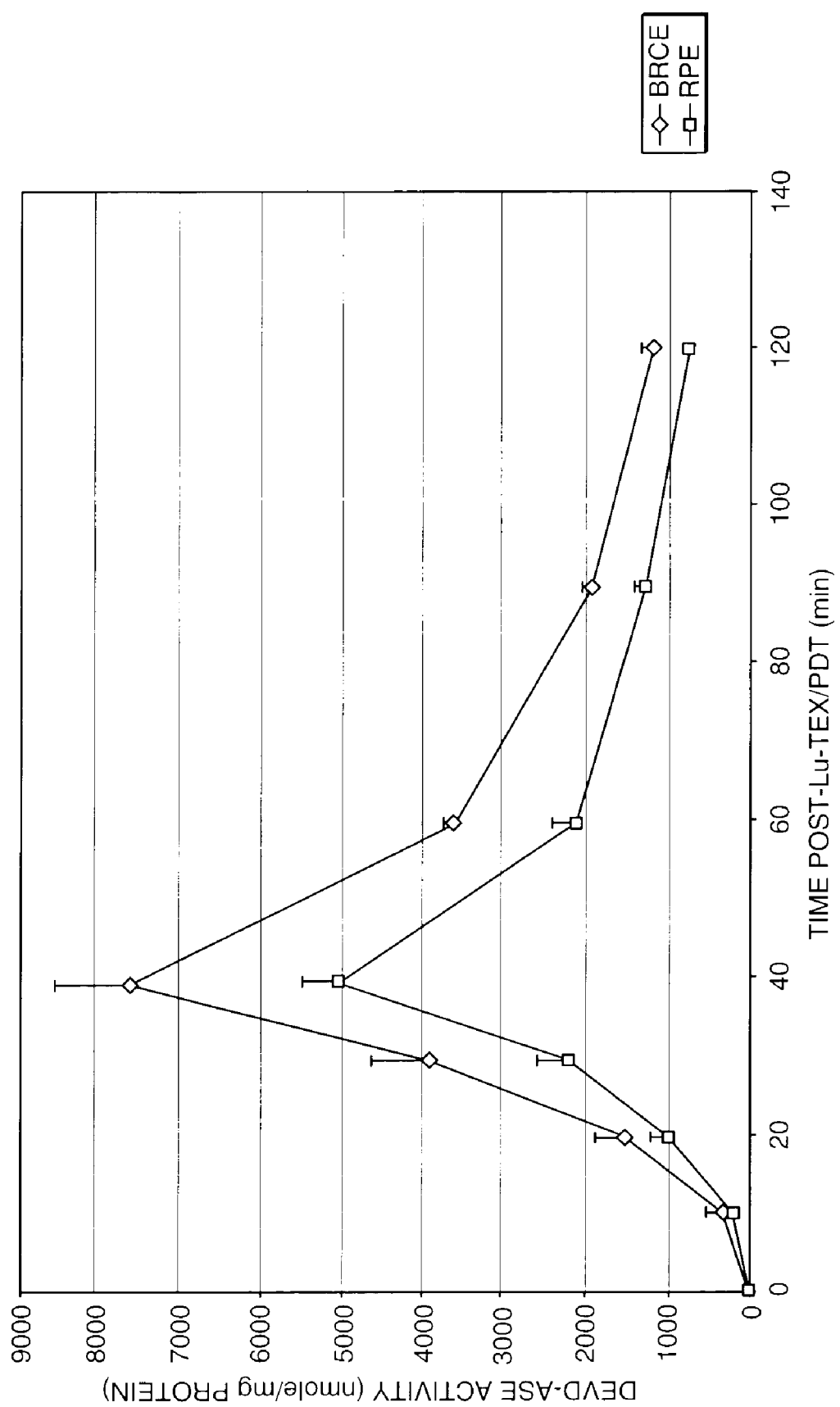
Figure 2C:
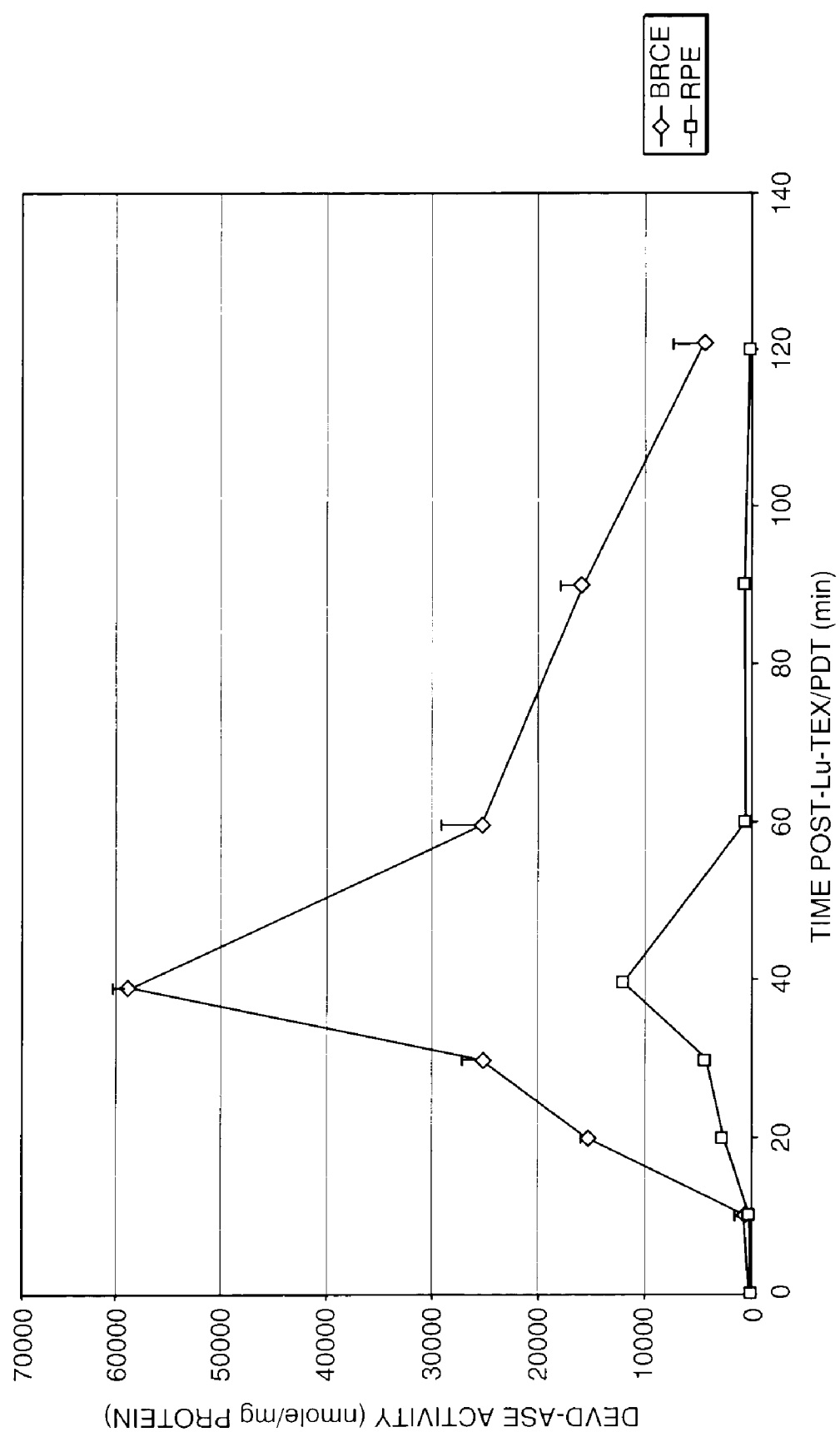

FIG. 2 illustrates the time course of Ac-DEVD-AFC cleavage after Lu-Tex/PDT at three different light doses in BRCE and RPE. FIGS. 2A, 2B and 2C represent data generated using light does of 10, 20 and 40 J/cm$^2$, respectively. The results show a rapid elevation of caspase 3-like activity immediately after Lu-Tex/PDT—as early as 10 min post-Lu-Tex/PDT and peaking at 40 min—in both BRCE and RPE cells and at all doses used. The rate of entry into apoptosis was time and dose-dependent in each cell line. However, the amount of caspase 3-like activation was always significantly higher in BRCE cells compared to RPE cells. Furthermore, whereas at 10 J/cm$^2$ and 20 J/cm$^2$, the amount of caspase 3-like activation increased by about 50% in BRCE cells as compared to RPE cells; at 40 J/cm$^2$ (equivalent to the LD$_{100}$ for BRCE cells), the levels in BRCE were 5-fold those in RPE cells.

Figure 3:
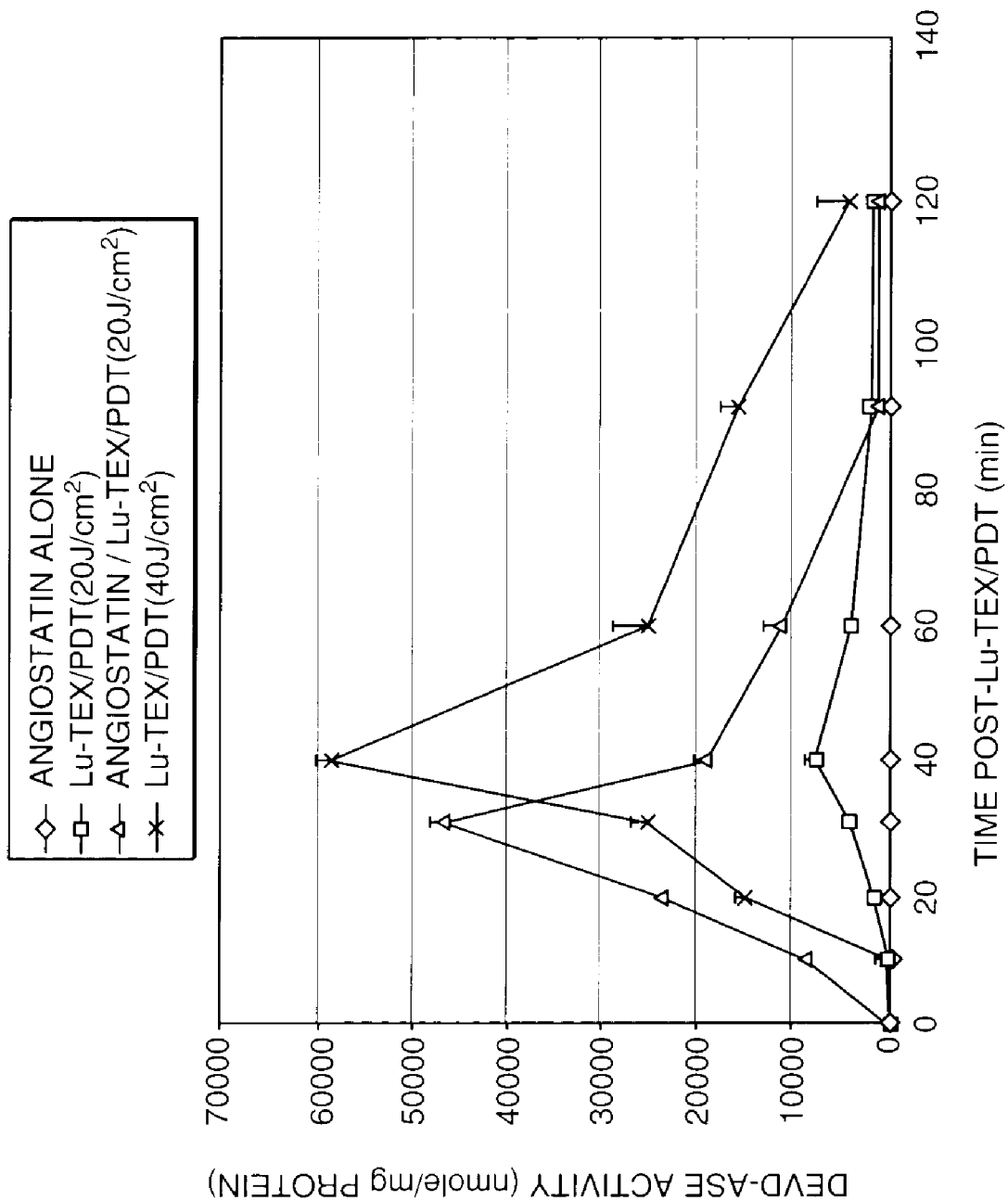
FIG. 3 is a graph showing Caspase 3-like activity in BRCE following Angiostatin/Lu-Tex/PDT versus Lu-Tex/PDT alone. BRCE were exposed to angiostatin (500 ng/ml) alone (diamonds), Lu-Tex/PDT (20 J/cm$^2$ (squares), 40 J/cm$^2$ (crosses)) alone and combination of angiostatin Lu-Tex/PDT (triangles). At the indicated times thereafter, cells were collected and lysed. Aliquots (50 µg of protein) were incubated with Ac-DEVD-AFC at 37° C. for 30 min. The amount of fluorochrome released was determined by comparison to a standard curve in lysis buffer and the data represent the means of three independent experiments.

In order to examine the effect of combining angiostatin and Lu-Tex/PDT on DEVD-ase activation in BRCE cells, cells were treated with angiostatin alone, Lu-Tex/PDT alone and angiostatin/Lu-Tex/PDT, following which caspase 3-like activity was assayed as described above. The results are summarized in FIG. 3. Fluences of 20 and 40 J/cm$^2$ were used, corresponding to LD$_{100}$ of combination angiostatin/Lu-Tex/PDT and Lu-Tex/PDT alone respectively. Results demonstrated that the combination of angiostatin/Lu-Tex/PDT induced a statistically significant increase of caspase 3-like activity as compared to Lu-Tex/PDT alone using a fluence of 20 J/cm$^2$ (FIG. 3). However, while both Lu-Tex/PDT (40J/cm$^2$) and the combination of angiostatin/Lu-Tex/PDT (20 J/cm$^2$) resulted in 100% lethality of BRCE cells; Lu-Tex/PDT (40J/cm$^2$) resulted in increased levels of caspase 3-like activity as compared to angiostatin/Lu-Tex/PDT (20 J/cm$^2$). As in the case of BRCE cells treated with Lu-Tex/PDT alone, the rate of entry into apoptosis of BRCE cells treated with combination of angiostatin/Lu-Tex/PDT was time-dependent. Nevertheless, the time courses differed significantly in that the induction of caspase 3-like activation occurred abruptly and more rapidly as a result of angiostatin/Lu-Tex/PDT, peaking at 30 minutes and reaching minimum levels at 90 minutes post-treatment.

EXAMPLE 4

Modulation of Bcl-2 Family Members in BRCE and RPE Cells after Lu-Tex/PDT

In order to evaluate the expression of Bcl-2 family members in BRCE and RPE cells after Lu-Tex/PDT, BRCE and RPE cells were subjected to Lu-Tex/PDT and the resultant cellular lysates subjected to Western blot analysis for detection of the anti-apoptotic Bcl-2, Bcl-x$_L$ markers, and the pro-apoptotic Bax and Bak markers.

Cell lysates were produced as described in Example 3. Sodium dodecyl sulfate-polyacrylamide gel electrophoresis of proteins was performed with 12% SDS-polyacrylamide gels. All samples were boiled in denaturing sample buffer, and equal amounts of proteins were loaded per lane. Proteins were separated at room temperature under reducing conditions at 120 V. Western blot transfer of separated proteins was performed at room temperature, using polyvinylidene fluoride membranes at 50 mA for 1 hr. To verify equal protein loading, blots were stained with 0.1% ponceau red (Sigma) diluted in 5% acetic acid. Afterwards, blots were blocked for 1 hr in Tris buffered saline (TBS; 10 mM Tris-HCl, pH 7.5, and 150 mM NaCl) containing 5% non-fat dried milk. Next, the membranes were probed with an appropriate dilution (1:250 to 1:1000) of primary antibody in TBS containing 2.5% non-fat dried milk for one and a half hours. Mouse polyclonal antibodies against Bcl-2, Bcl-x$_L$, Bax and Bak were purchased from Pharmingen. After incubation with primary antibody, the blots were washed for 30 minutes with frequent changes of TBS, blocked in 1% non-fat dried milk in TBS for 30 minutes, followed by incubation in a peroxidase-coupled secondary antibody for 1 hour in TBS containing 1% non-fat dried milk. The blots were washed for 1 hour with frequent changes of TBST (TBS, 0.1% Tween). Immunoblot analysis was performed using enhanced chemiluminescence plus Western blotting detection reagents (Amersham, Pharmacia Biotec Piscataway, N.J.) followed by exposure to x-ray film (ML Eastman Kodak, Rochester, N.Y.).

Results showed a differential expression of members of Bcl-2 family members in BRCE and RPE cells. Specifically, Bcl-2 and Bax were detected in BRCE cells whereas Bcl-x$_L$ and Bak were detected in RPE cells (Table 2). After Lu-Tex/PDT at LD$_{50}$, downregulation of Bcl-2 and upregulation of Bax was observed in BRCE cells resulting in an increase of the cellular ratio of Bax to Bcl-2 protein. In RPE cells, there was an upregulation of both Bcl-xL and Bak up to 4 hours post-PDT, after which, Bcl-x$_L$ levels reached a plateau, and Bak level started to decline. The upregulation of Bax in BRCE cells appeared to be dose-dependent, however, the upregulation of its pro-apoptotic counterpart Bak in RPE exhibited dose-dependence only until 20 J/cm$^2$; after which it began to decline.

Lu-Tex/PDT induced caspase 3-like activation in both BRCE and RPE cells in a dose- and time-dependent fashion, suggesting that apoptosis is a mediator of Lu-Tex/PDT cytotoxicity in these cell lines. Furthermore, the data indicate that Lu-Tex/PDT induced apoptosis in BRCE cells through the modulation of Bcl-2 and Bax in a dose- and time-dependent fashion, and in RPE cells through the modulation of Bcl-x$_L$ and Bak. As a result, Lu-Tex/PDT may cause different modes of death in each of the different cell types.

TABLE 2

Summary of Immunodetection of $Bcl_2$ Family Members in BRCE and RPE Cells

| $Bcl_2$ family member | Cell Line | |
|---|---|---|
| | BRCE | RPE |
| $Bcl_2$ | + | − |
| $Bcl-x_L$ | − | + |
| Bax | + | − |
| Bak | − | + |

Detectable(+) or undetectable(−).

After incremental PDT doses, the pro-apoptotic Bak was upregulated in RPE cells until 20 $J/cm^2$ following which Bak levels started declining despite an increase of PDT dose to 40 $J/cm^2$. Without wishing to be bound by theory, it is possible that a protective survival response is mounted in RPE cells at these lethal doses to counteract the apoptotic trigger. Such a hypothesis is further supported by the histologic evidence of RPE cells recovery post-PDT in vivo (Kramer et al. (1996) OPHTHALMOLOGY 103(3): 427438, Husain et al. (1999) INVEST OPHTHALMOL VISL SCI. 40: 2322–31) and by reports from other investigators showing that overexpression of anti-apoptotic $Bcl_2$ family members render cells partially resistant to PDT (He et al. (1996) PHOTOCHEMISTRY AND PHOTOBIOLOGY 64: 845–852) and inhibits the activation of caspase-3 after PDT (Granville et al. (1998) FEBS 422: 151–154).

The data show that the combination of angiostatin to Lu-Tex/PDT in BRCE cells resulted in an increase in DEVD-ase activity compared with a same dose of Lu-Tex/PDT applied alone. This suggests that the potentiating action of angiostatin on the effect of Lu-Tex/PDT in BRCE cells proceeds through apoptosis. However, the time course of caspase 3-like activity for angiostatin/Lu-Tex/PDT differed from that of Lu-Tex/PDT alone in that it proceeded faster without latency and peaked as soon as 20 minutes after Lu-Tex/PDT. The latter may be explained on the basis that perhaps the apoptotic cascade was already primed by pre-incubation with angiostatin first, and thus the application of Lu-Tex/PDT benefited from an already lowered threshold of activation to rapidly amplify the apoptotic response. However, this does not exclude the possibility of the interplay of more than one apoptotic pathway, especially since PDT is known to initiate cytotoxicity through the generation of reactive oxygen species (Weishaupt et aL (1976) supra) whereas angiostatin was recently shown to act on human endothelial cells by binding to the α-subunit of adenosine triphosphate synthase present on the cell surface (Moser et al. (1999) PROC NATL ACAD SCI USA 96: 2811–2816). Furthermore, whereas angiostatin/Lu-Tex/PDT (20 $J/cm^2$) resulted in a 100% lethality of BRCE cells as did Lu-Tex/PDT (40 $J/Cm^2$) alone, the levels of DEVD-ase activation were significantly higher in the former regimen. This supports the theory that Lu-Tex/PDT and Angiostatin/Lu-Tex/PDT operate through different apoptotic pathways in BRCE cells.

EXAMPLE 5

Targeted Delivery of Photosensitizer to the Choroidal Neovasculature

It is contemplated that a photosensitizer can be directed to the CNV endothelium by coupling the photosensitizer to a neovascular endothelium binding moieties in order to increase the efficacy and lower the toxicity of PDT. Several targeting molecules may be used to target photosensitizers to the neovascular endothelium. The α-v integrins, in particular α-v β-3 and α-v β-5 integrins, appear to be expressed in ocular neovascular tissue, in both clinical specimens and experimental models (Corjay et al. (1997) supra; Friedlander et al. (1995) supra). Cyclic peptide antagonists of these integrins have been used to inhibit neovascularization in experimental models (Friedlander et al. (1996) PROC. NATL. ACAD. SCI. USA 93:9764–9769). A peptide motif ACD-CRGDCFC (SEQ ID NO: 2)—also called RGD-4C—was identified that selectively binds to human α-v integrins and accumulates in tumor neovasculature more effectively than other angiogenesis targeting peptides (Arap et al. (1998) NATURE 279:377–380). Another potential targeting molecule is an antibody for vascular endothelial growth factor receptor (VEGF-2R). Clinical and experimental evidence strongly supports a role for VEGF in ocular neovascularization, particularly ischemia-associated neovascularization (Adamis et al. (1996) ARCH. OPHTHALMOL. 114:66–71; Tolentino et al. (1996) ARCH. OPHTHALMOL. 114:964–970; Tolentino et al. (1996) OPHTHALMOLOGY 103:1820–1828). Antibody to the VEGF receptor (VEGFR-2 also known as KDR) can be expected to bind preferentially to neovascular endothelium.

Experimental Design

The photosensitizer Verteporfin (QLT Phototherapeutics, Inc., Vancouver BC) or Lutetium Texaphryin (Alcon Laboratories, Fort Worth, Tex.) will be coupled to a targeting moiety, for example, an RGD-4C peptide, or an anti-VEGF receptor antibody using standard coupling chemistries. The spectral characteristics (emission & excitation) of the resulting photosensitizer complex can be measured in vitro. Subsequently, in vitro studies can be carried out using BRCE and RPE cells, to assess cellular uptake and phototoxicity following PDT. Experiments may address PDT treatment parameters including optimal timing as well as drug and light dosimetry for selective phototoxicity in vitro. Then, the efficacy and selectivity of PDT using the bound photosensitizer in vivo in the rat model of CNV can be tested. The results of PDT with photosensitizer comprising the targeting molecule may then be compared to the results of PDT with the same photosensitizer lacking the targeting molecule.

CNV can be induced in animals using a krypton laser, and documented by digital fundus fluorescein angiography. More specifically, the laser injury model in the rat is a modification of a similar model in the monkey (Dobi et al. (1989) ARCH. OPHTHALMOL. 107:264–269; Ryan (1982) ARCH. OPHTHALMOL. 100:1804–1809; Tobe et al. (1994) J. JPN. OPHTHALMOL. SOC. 98:837–845). Briefly, 5–6 high intensity krypton laser burns (100 μm spot size, 0.1-second duration, 160 mW) can be placed in a peripapillary fashion. CNV as evidenced by hyperfluorescence and late leakage can be documented using digital fluorescein angiography and is expected to develop in at least 60% of the lesions within 2–3 weeks of laser injury.

PDT can then be performed over areas of CNV and normal choroid and the effects assessed angiographically and histologically. More specifically, PDT may be carried out using tail vein injection of the photosensitizer either containing or lacking a targeting molecule, followed by laser irradiation of the treatment area. PDT may also be applied to areas of CNV in one eye and to areas of normal choroid in the fellow eye. Photosensitizer and laser parameters will be based on previous experiments using Verteporfin and Lu-Tex in the monkey model, as well as some preliminary dosimetry in the rat model.

The efficacy of PDT can be assessed as follows:

(a) Efficacy of CNV closure. Effective closure of CNV can be assessed by the absence of leakage from CNV via fluorescein angiography 24 hours after PDT. This methodology has been well established in the laser injury in the monkey. Histopathology can be carried out using light microscopy.

(b) Selectivity of Effect. Since CNV in this model develops in an area of laser injury, it is difficult to assess the effects of PDT on retina and choroid when areas of CNV are treated. Therefore, to demonstrate the selectivity of PDT to CNV, PDT may also be applied to areas of normal retina and choroid and a published histopathologic grading scheme used to quantify damage to RPE, photoreceptors, retinal and choroidal vessels (Kramer et al. (1996) OPHTHALMOLOGY 103:427–438).

(c) Comparison of the Effects of PDT versus combined PDT regimens. The effects of PDT may be compared between groups of CNV animals treated with PDT using photosensitizer alone, and groups receiving modified PDT (i.e. targeted photosensitizer). PDT may be applied to the CNV and normal areas. First, it may be determined if CNV closure occurs at the same light dose (fluence $J/cm^2$) using the modified PDT as with PDT alone. Then, at the identified light dose, the effects of modified PDT, and PDT alone, on normal choroid may be compared. As an example, using the targeted photosensitizer, one may be able to achieve closure of CNV at a lower fluence than with unbound photosensitizer and at this fluence one may find much less damage to the RPE in normal areas treated with PDT using targeted photosensitizer.

EXAMPLE 6

Combined Effects of Targeted Pro-Apoptotic Peptides and PDT for Choroidal Neovascularization Treatment Experiments have shown that PDT induces cell death in endothelial cells by apoptosis and that its toxicity towards the RPE also proceeds by programmed cell death. Different apoptotic pathways appear to be triggered by PDT in BRCE and RPE cells. It is contemplated that by specifically priming the apoptotic machinery of neovascular capillary endothelial cells prior to PDT it may be possible to increase their sensitivity to PDT. This approach may reduce the light dose (fluence) required to achieve CNV closure and thereby decrease the effect on the surrounding cells such as RPE cells.

Studies have shown the efficacy of targeted pro-apoptotic peptides in anti-cancer activity in significantly reducing the tumor size (Ellerby et al. (1999) supra). These targeted pro-apoptotic conjugates were comprised of two functional domains: an antimicrobial peptide (KLAKLAKKLAKLAK; SEQ ID NO: 1) with low mammalian toxicity and an angiogenic homing peptide (RGD-4C). The antibacterial peptide preferentially disrupts prokaryotic membranes and eukaryotic mitochondrial membranes rather than eukaryotic plasma membranes (Ellerby et al. (1999) supra). Thus the chimeric peptide, therefore, may have the means to enter the cytosol of targeted cells, where it induces mitochondrial-dependent apoptosis. Endothelial cells primed with these conjugates are expected to be more susceptible to PDT.

Experimental Design

Peptides of interest will first be tested in vitro in BRCE and RPE cells to ascertain specificity and efficacy. Then, the pro-apoptotic peptide/PDT regimen may be assessed in vitro, and then compared with PDT alone and peptide alone in both BRCE and RPE cells. BRCE and RPE cells may be grown using standard tissue culture techniques. The ApoAlert assay kit (Clonetech) may be used to assay for caspase-3 like activity in cells post-treatment. This colorimetric assay follows the chromophore p-nitroanilide (pNA) arising from cleavage of the substrate DEVD-pNA. DEVD-pNA is a known substrate for active caspase-3 and can be added to cellular extracts prepared at different time points after treatment, and samples can be analyzed to assess caspase-3 activity.

Thereafter, experiments may be carried out to test the efficacy and selectivity of targeted pro-apoptotic peptide in vivo in the rat model of CNV. Targeted pro-apoptotic peptides may be injected intravenously 4 hours prior to PDT. PDT may be performed over areas of CNV and in normal eyes, comparing the effect on CNV closure of PDT alone with PDT after pro-apoptotic peptide, and comparing the selectivity in normal choroid as described in Example 5.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

Each of the patent documents and scientific publications disclosed hereinabove is expressly incorporated herein by reference.

What is claimed is:

1. A method of enhancing closure of unwanted choroidal neovasculature comprising endothelial cells in a mammal, the method comprising the steps of:
   (a) administering to the mammal an anti-angiogenesis factor in an amount sufficient to permit an effective amount to localize in the choroidal neovasculature, wherein the anti-angiogenesis factor is selected from the group consisting of angiostatin and an antibody that binds preferentially to vascular endothelial growth factor;
   (b) administering to the mammal after step (a) an amount of a tetrapyrrole derivative photosensitizer sufficient to permit an effective amount to localize in the choroidal neovasculature, wherein the photosensitizer is selected from the group consisting of lutetium texaphyrin and benzoporphyrin derivative; and
   (c) irradiating the choroidal neovasculature with laser light such that the light is absorbed by the photosensitizer so as to damage endothelial cells and occlude the choroidal neovasculature, wherein the occlusion caused by step (a) is synergistic with the occlusion caused by steps (b) and (c) thereby enhancing closure of the unwanted choroidal neovasculature.

2. The method of claim 1, wherein the mammal is a primate.

3. The method of claim 2, wherein the primate is a human.

4. The method of claim 1, wherein the method more selectively occludes choroidal neovasculature relative to the same treatment lacking administration of the anti-angiogenesis factor.

5. The method of claim 1, wherein the method ameliorates the symptoms of age-related macular degeneration.

6. A method of enhancing closure of unwanted choroidal neovasculature comprising endothelial cells in a mammal, the method comprising the steps of:
   (a) administering to the mammal an anti-angiogenesis factor in an amount sufficient to permit an effective amount to localize in the choroidal neovasculature, wherein the anti-angiogenesis factor is selected from the group consisting of angiostatin and an antibody that binds preferentially to vascular endothelial growth factor;
   (b) administering to the mammal after step (a) an amount of a tetrapyrrole derivative photosensitizer sufficient to permit an effective amount to localize in the choroidal neovasculature, wherein the photosensitizer is selected from the group consisting of lutetium texaphyrin and benzoporphyrin derivative; and
   (c) irradiating the choroidal neovasculature with laser tight such that the light is absorbed by the photosensitizer so as to occlude the choroidal neovasculature, wherein damage to the endothelial cells resulting from the combination of steps (a), (b), and (c) is greater than that resulting only from the sum of steps (a), (b) and (c).

7. The method of claim 6, wherein the mammal is a primate.

8. The method of claim 7, wherein the primate is a human.

9. The method of claim 6, wherein occlusion of the choroidal neovasculature resulting from steps (a), (b), and (c) is greater than that resulting from steps (b) and (c) alone.

10. The method of claim 6, wherein the method more selectively occludes choroidal neovasculature relative to the same treatment lacking administration of the anti-angiogenesis factor.

11. The method of claim 6, wherein the method ameliorates the symptoms of age-related macular degeneration.

* * * * *

SEQUENCE LISTING

<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: Synthetic sequence -continued

```
<400> SEQUENCE: 1

Lys Leu Ala Lys Leu Ala Lys Lys Leu Ala Lys Leu Ala Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic sequence

<400> SEQUENCE: 2

Ala Cys Asp Cys Arg Gly Asp Cys Phe Cys
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic sequence

<400> SEQUENCE: 3

Asp Glu Val Asp
1
```